(12) United States Patent
Ito et al.

(10) Patent No.: US 10,517,512 B2
(45) Date of Patent: Dec. 31, 2019

(54) SWING DIAGNOSIS METHOD, RECORDING MEDIUM, SWING DIAGNOSIS APPARATUS, AND SWING DIAGNOSIS SYSTEM

(71) Applicant: SEIKO EPSON CORPORATION, Tokyo (JP)

(72) Inventors: Tsuyoshi Ito, Suwa (JP); Kenya Kodaira, Azumino (JP); Norihisa Hagiwara, Hachioji (JP); Kazuhiro Ito, Yokohama (JP)

(73) Assignee: SEIKO EPSON CORPORATION, Tokyo (JP)

( * ) Notice: Subject to any disclaimer, the term of this patent is extended or adjusted under 35 U.S.C. 154(b) by 409 days.

(21) Appl. No.: 15/211,619

(22) Filed: Jul. 15, 2016

(65) Prior Publication Data
US 2017/0028282 A1 Feb. 2, 2017

(30) Foreign Application Priority Data
Jul. 28, 2015 (JP) ................. 2015-148639

(51) Int. Cl.
*A63B 69/36* (2006.01)
*A61B 5/11* (2006.01)

(52) U.S. Cl.
CPC .................. *A61B 5/1121* (2013.01)

(58) Field of Classification Search
CPC .......... A61B 5/1121; A61B 2562/0219; A61B 5/6824; A61B 5/681; A61B 5/7455; A61B 5/6895; A61B 2503/10; G06Q 10/0639; G09B 19/0038; H04M 1/7253

USPC ................ 473/594, 614, 212, 221, 223, 409
See application file for complete search history.

(56) References Cited

U.S. PATENT DOCUMENTS

| | | | | |
|---|---|---|---|---|
| 3,314,051 A | * | 4/1967 | Wilcox ................ | G06F 3/0489 101/93 |
| 3,469,243 A | * | 9/1969 | Willcox ................ | G06F 3/0489 340/7.21 |
| 3,484,768 A | * | 12/1969 | Willcox ................ | G06F 3/0489 226/9 |
| 3,523,281 A | * | 8/1970 | Willcox ................ | G06F 3/0489 375/219 |
| 7,219,033 B2 | * | 5/2007 | Kolen .................... | G01C 19/00 702/150 |
| 2005/0215336 A1 | | 9/2005 | Ueda et al. | |
| 2011/0054752 A1 | * | 3/2011 | Arai ...................... | F16D 48/062 701/67 |
| 2011/0224012 A1 | * | 9/2011 | Hashimoto ......... | A63B 69/3632 473/223 |
| 2012/0088544 A1 | * | 4/2012 | Bentley .................. | A63F 13/06 455/556.1 |

(Continued)

FOREIGN PATENT DOCUMENTS

| | | |
|---|---|---|
| JP | 2004-135908 A | 5/2004 |
| JP | 2005-270500 A | 10/2005 |

(Continued)

*Primary Examiner* — Nini F Legesse
(74) *Attorney, Agent, or Firm* — Oliff PLC

(57) ABSTRACT

A swing diagnosis method includes a procedure of calculating levels of a plurality of items including a first item regarding at least one of a backswing and a downswing, and a second item regarding impact on the basis of data regarding a swing, and a procedure of outputting information regarding the levels of the plurality of items.

21 Claims, 25 Drawing Sheets

(56) References Cited

U.S. PATENT DOCUMENTS

| | | | |
|---|---|---|---|
| 2013/0029791 A1* | 1/2013 | Rose | G09B 19/0038 473/409 |
| 2014/0135139 A1 | 5/2014 | Shibuya et al. | |
| 2014/0376293 A1* | 12/2014 | West | H02M 1/126 363/131 |
| 2014/0379293 A1 | 12/2014 | Sato | |
| 2014/0379294 A1 | 12/2014 | Shibuya et al. | |
| 2014/0379295 A1 | 12/2014 | Sato et al. | |
| 2015/0012240 A1 | 1/2015 | Sato | |
| 2015/0111657 A1* | 4/2015 | Shibuya | G06K 9/00342 473/223 |
| 2015/0119158 A1* | 4/2015 | Sato | G09B 19/0038 473/223 |
| 2016/0001127 A1* | 1/2016 | Sato | A63B 69/3632 473/223 |
| 2017/0028251 A1 | 2/2017 | Ito et al. | |
| 2017/0028252 A1 | 2/2017 | Ito et al. | |
| 2017/0028254 A1 | 2/2017 | Ito et al. | |
| 2017/0028283 A1 | 2/2017 | Ito et al. | |
| 2017/0036082 A1 | 2/2017 | Kodaira et al. | |

FOREIGN PATENT DOCUMENTS

| | | |
|---|---|---|
| JP | 2008-073210 A | 4/2008 |
| JP | 2014-097104 A | 5/2014 |
| JP | 2015-002910 A | 1/2015 |
| JP | 2015-002911 A | 1/2015 |
| JP | 2015-002912 A | 1/2015 |
| JP | 2015-009008 A | 1/2015 |
| JP | 2015-013007 A | 1/2015 |
| JP | 2015-073821 A | 4/2015 |
| JP | 2015-073822 A | 4/2015 |
| JP | 2016-013302 A | 1/2016 |
| JP | 2017-023636 A | 2/2017 |
| JP | 2017-023638 A | 2/2017 |
| JP | 2017-023639 A | 2/2017 |
| JP | 2017-023640 A | 2/2017 |
| JP | 2017-023643 A | 2/2017 |
| JP | 2017-029460 A | 2/2017 |

\* cited by examiner

PHYSICAL INFORMATION

HEIGHT [cm]    170

SEX    ⦿MALE ○FEMALE

AGE    36

COUNTRY    JAPAN

GOLF CLUB INFORMATION

CLUB LENGTH [cm]    115

NUMBER    1W

FIG. 5

| DATE AND TIME | GOLF CLUB | HEAD SPEED | FACE ANGLE | CLUB PATH (INCIDENCE ANGLE) | SHAFT AXIS ROTATION (TOP) | GRIP DECELERATION RATIO | GRIP DECELERATION TIME RATIO |
|---|---|---|---|---|---|---|---|
| ☑ 2015/07/01 00:01:00 PM | 1W | 40.0 m/s | 4.0 deg | −1.0 deg | 70.0 deg | 30.0 % | 14.0 % |
| ☐ 2015/07/01 00:59:00 PM | 1W | 39.0 m/s | 3.9 deg | −0.9 deg | 69.0 deg | 29.0 % | 13.0 % |
| ☐ 2015/07/01 00:58:00 PM | 1W | 41.0 m/s | 4.1 deg | −1.1 deg | 71.0 deg | 31.0 % | 15.0 % |
| ☐ 2015/07/01 00:57:00 PM | 7I | 38.0 m/s | 3.8 deg | −0.8 deg | 68.0 deg | 28.0 % | 12.0 % |
| ☐ 2015/07/01 00:56:00 PM | 7I | 37.0 m/s | 3.7 deg | −0.7 deg | 67.0 deg | 27.0 % | 11.0 % |

OK

| V ZONE SCORE TABLE | | HEAD POSITION AT HALFWAY DOWN | | | | |
|---|---|---|---|---|---|---|
| | | A | B | C | D | E |
| HEAD POSITION AT HALFWAY BACK | A | pv1 | pv2 | pv3 | pv4 | pv5 |
| | B | pv6 | pv7 | pv8 | pv9 | pv10 |
| | C | pv11 | pv12 | pv13 | pv14 | pv15 |
| | D | pv16 | pv17 | pv18 | pv19 | pv20 |
| | E | pv21 | pv22 | pv23 | pv24 | pv25 |

FIG. 25

| ROTATION SCORE TABLE | | FACE ANGLE φ [deg] | | | | | | |
|---|---|---|---|---|---|---|---|---|
| | | CLOSE | | | SQUARE | OPEN | | |
| | | LESS THAN φ1 | φ1~φ2 | φ2~φ3 | φ3~φ4 | φ4~φ5 | φ5~φ6 | φ6 OR MORE |
| SHAFT AXIS ROTATION ANGLE θtop [deg] | LESS THAN θ1 | pr1 | pr2 | pr3 | pr4 | pr5 | pr6 | pr7 |
| | θ1~θ2 | pr8 | pr9 | pr10 | pr11 | pr12 | pr13 | pr14 |
| | θ2~θ3 | pr15 | pr16 | pr17 | pr18 | pr19 | pr20 | pr21 |
| | θ3~θ4 | pr22 | pr23 | pr24 | pr25 | pr26 | pr27 | pr28 |
| | θ4 OR MORE | pr29 | pr30 | pr31 | pr32 | pr33 | pr34 | pr35 |

343

$\overset{344}{\swarrow}$

| IMPACT SCORE TABLE | | CLUB PATH (INCIDENCE ANGLE) $\psi$[deg] | | | | |
|---|---|---|---|---|---|---|
| | | LESS THAN $\psi1$ | $\psi1\sim\psi2$ | $\psi2\sim\psi3$ | $\psi3\sim\psi4$ | $\psi4$ OR MORE |
| RELATIVE FACE ANGLE $\eta$ [deg] | LESS THAN $\eta1$ | pi1 | pi2 | pi3 | pi4 | pi5 |
| | $\eta1\sim\eta2$ | pi6 | pi7 | pi8 | pi9 | pi10 |
| | $\eta2\sim\eta3$ | pi11 | pi12 | pi13 | pi14 | pi15 |
| | $\eta3\sim\eta4$ | pi16 | pi17 | pi18 | pi19 | pi20 |
| | LESS THAN $\eta4$ | pi21 | pi22 | pi23 | pi24 | pi25 |

FIG. 26

$\overset{345}{\swarrow}$

| SPEED SCORE TABLE | | 1 POINT | 2 POINTS | 3 POINTS | 4 POINTS | 5 POINTS |
|---|---|---|---|---|---|---|
| MALE | DRIVER | LESS THAN vh1 | vh1~vh2 | vh2~vh3 | vh3~vh4 | vh4 OR MORE |
| | IRON | LESS THAN vh5 | vh5~vh6 | vh6~vh7 | vh7~vh8 | vh8 OR MORE |
| FEMALE | DRIVER | LESS THAN vh11 | vh11~vh12 | vh12~vh13 | vh13~vh14 | vh14 OR MORE |
| | IRON | LESS THAN vh15 | v15~vh16 | vh16~vh17 | vh17~vh18 | vh18 OR MORE |

FIG. 27

$\overset{346}{\swarrow}$

| SWING EFFICIENCY SCORE TABLE | | GRIP DECELERATION TIME RATIO $R_T$ [%] | | | | | |
|---|---|---|---|---|---|---|---|
| | | nup1 OR MORE | nup1~nup2 | nup2~nup3 | nup3~nup4 | nup4~nup5 | LESS THAN nup5 |
| GRIP DECELERATION RATIO $R_v$ [%] | nu1 OR MORE | ps1 | ps2 | ps3 | ps4 | ps5 | ps6 |
| | nu1~nu2 | ps7 | ps8 | ps9 | ps10 | ps11 | ps12 |
| | nu2~nu3 | ps13 | ps14 | ps15 | ps16 | ps17 | ps18 |
| | nu3~nu4 | ps19 | ps20 | ps21 | ps22 | ps23 | ps24 |
| | nu4~nu5 | ps25 | ps26 | ps27 | ps28 | ps29 | ps30 |
| | LESS THAN nu5 | ps31 | ps32 | ps33 | ps34 | ps35 | ps36 |

FIG. 28

SWING DIAGNOSIS METHOD, RECORDING MEDIUM, SWING DIAGNOSIS APPARATUS, AND SWING DIAGNOSIS SYSTEM

BACKGROUND

1. Technical Field

The present invention relates to a swing diagnosis method, a recording medium, a swing diagnosis apparatus, and a swing diagnosis system.

2. Related Art

JP-A-2004-135908 discloses a measurement system provided with sensor means for detecting passing of a golf club head which is swung downward in order to hit a golf ball; an impact camera which captures an image of impact; a first ball measurement camera and a second ball measurement camera which are set at positions separated from each other by a predetermined distance along a flight line (flight trajectory) of a hit ball in order to capture images of the hit ball after the impact; a performance measurement device of the golf club; and a monitor which displays a movement state of the golf ball. The measurement system analyzes a movement state of the hit golf ball on the basis of the images, and displays the movement state of the golf ball as a radar chart. Therefore, according to the measurement system, it is possible to easily evaluate performance of a golf club on the basis of a movement state of the golf ball.

However, the measurement system disclosed in JP-A-2004-135908 displays a movement state of the hit golf ball, that is, data after impact, as a radar chart, and thus it is hard to understand features of a swing till the impact even if the radar chart is observed.

SUMMARY

An advantage of some aspects of the invention is to provide a swing diagnosis method, a recording medium, a swing diagnosis apparatus, and a swing diagnosis system, capable of clearly showing features of a swing till impact.

The invention can be implemented as the following forms or application examples.

APPLICATION EXAMPLE 1

A swing diagnosis method according to this application example includes a procedure of calculating levels of a plurality of items including a first item regarding at least one of a backswing and a downswing, and a second item regarding impact on the basis of data regarding a swing; and a procedure of outputting information of the levels of the plurality of items.

The data regarding the swing may be, for example, measured data of acceleration or angular velocity regarding the swing, and may be analysis information including values of indexes indicating features of the swing, obtained by analyzing the measured data. Alternatively, the data regarding the swing may be data in which some or all values of indexes indicating features of the swing are pseudo-values. The data regarding the swing may be data based on an output signal from an inertial sensor measuring acceleration or angular velocity regarding the swing.

According to the swing diagnosis method of this application example, it is possible to grade and diagnose a feature of the backswing or the downswing by calculating a level of the first item regarding at least one of the backswing and the downswing on the basis of the data regarding the swing. According to the swing diagnosis method of the application example, it is also possible to grade and diagnose a feature of the swing at impact by calculating a level of the second item regarding the impact on the basis of the data regarding the swing. According to the swing diagnosis method of the application example, it is possible to grade and clearly show features of the swing till the impact by outputting level information of the plurality of items including the first item and the second item.

APPLICATION EXAMPLE 2

In the swing diagnosis method according to the application example, the first item may include an item indicating a relationship between at least one virtual plane, and a position of a ball hitting portion of an exercise appliance at a first timing during the backswing and a position of the ball hitting portion at a second timing during the downswing.

The first timing may be the time at which a long axis direction of the exercise appliance becomes a direction along a horizontal direction during the backswing. The second timing may be the time at which the long axis direction of the exercise appliance becomes a direction along the horizontal direction during the downswing.

The exercise appliance is a tool used for a swing, and may be, for example, a golf club, a tennis racket, a baseball bat, or a hockey stick.

According to the swing diagnosis method of this application example, it is possible to grade and clearly show a feature of the swing based on a relationship between the virtual plane and positions of the ball hitting portion of the exercise appliance at desired timings during the backswing and the downswing.

APPLICATION EXAMPLE 3

In the swing diagnosis method according to the application example, the at least one virtual plane may include a first virtual plane that is specified on the basis of a first axis along a target hit ball direction, and a second axis along a longitudinal direction of the exercise appliance before starting the backswing; and a second virtual plane that forms a first angle with the first virtual plane.

The target hit ball direction may be a direction in a reference plane (for example, a horizontal plane).

According to the swing diagnosis method of this application example, it is possible to grade and clearly show a feature of the swing based on relationships among the first virtual plane, the second virtual plane, and positions of the ball hitting portion of the exercise appliance at desired timings during the backswing and the downswing.

APPLICATION EXAMPLE 4

In the swing diagnosis method according to the application example, the first item may include an item regarding the efficiency of the swing.

According to the swing diagnosis method of this application example, it is possible to grade and clearly show a feature of the swing based on the efficiency of the swing.

APPLICATION EXAMPLE 5

In the swing diagnosis method according to the application example, the item regarding the swing efficiency may be an item indicating a relationship between a deceleration amount and a deceleration period of a holding portion of the exercise appliance in the downswing.

According to the swing diagnosis method of this application example, it is possible to grade and clearly show a feature of the swing based on a deceleration amount and a deceleration period of the holding portion of the exercise appliance in the downswing.

APPLICATION EXAMPLE 6

In the swing diagnosis method according to the application example, the second item may include an item indicating a relationship between an incidence angle of a ball hitting portion of an exercise appliance and an inclination of the ball hitting portion at impact.

According to the swing diagnosis method of this application example, it is possible to grade and clearly show a feature of the swing based on a relationship between an incidence angle of the ball hitting portion of the exercise appliance and an inclination of the ball hitting portion at impact.

APPLICATION EXAMPLE 7

In the swing diagnosis method according to the application example, the second item may include an item regarding a speed of an exercise appliance at impact.

According to the swing diagnosis method of this application example, it is possible to grade and clearly show a feature of the swing based on a speed of the exercise appliance at impact.

APPLICATION EXAMPLE 8

In the swing diagnosis method according to the application example, the plurality of items may further include a third item regarding the time at which the backswing transitions to the downswing and the impact.

According to the swing diagnosis method of this application example, it is also possible to grade and diagnose a feature of the swing in which the time of starting the downswing and the time of finishing the downswing are taken into particular consideration by calculating a level of the third item regarding the time at which the backswing transitions to the downswing, and the impact on the basis of the data regarding the swing. According to the swing diagnosis method of the application example, it is possible to grade and clearly show features of the swing till the impact by outputting level information of a plurality of items including the first item, the second item, and the third item.

APPLICATION EXAMPLE 9

In the swing diagnosis method according to the application example, the third item may include an item indicating a relationship between a rotation angle about a rotation axis of an exercise appliance at a timing at which the backswing transitions to the downswing with a longitudinal direction of the exercise appliance as the rotation axis, and an inclination of a ball hitting portion of the exercise appliance at a timing of the impact.

According to the swing diagnosis method of this application example, it is possible to grade and clearly show a feature of the swing based on a relationship between a rotation angle about a longitudinal direction of the exercise appliance at the time of starting the downswing and an inclination of the ball hitting portion of the exercise appliance at impact.

APPLICATION EXAMPLE 10

In the swing diagnosis method according to the application example, the levels may be scores.

According to the swing diagnosis method of this application example, it is possible to digitalize and clearly show a feature of the swing till the impact.

APPLICATION EXAMPLE 11

A swing diagnosis program according to this application example causes a computer to execute a procedure of calculating levels of a plurality of items including a first item regarding at least one of a backswing and a downswing, and a second item regarding impact on the basis of data regarding a swing; and a procedure of outputting information of the levels of the plurality of items.

APPLICATION EXAMPLE 12

A recording medium according to this application example records a swing diagnosis program causing a computer to execute a procedure of calculating levels of a plurality of items including a first item regarding at least one of a backswing and a downswing, and a second item regarding impact on the basis of data regarding a swing; and a procedure of outputting information of the levels of the plurality of items.

APPLICATION EXAMPLE 13

A swing diagnosis apparatus according to this application example includes a level calculation section that calculates levels of a plurality of items including a first item regarding at least one of a backswing and a downswing, and a second item regarding impact on the basis of data regarding a swing; and an output section that outputs information of the levels of the plurality of items.

According to the swing diagnosis program, the recording medium, or the swing diagnosis apparatus of these application examples, it is possible to grade and diagnose a feature of the backswing or the downswing by calculating a level of the first item regarding at least one of the backswing and the downswing on the basis of the data regarding the swing. According to the application example, it is also possible to grade and diagnose a feature of the swing at impact by calculating a level of the second item regarding the impact on the basis of the data regarding the swing. According to the application example, it is possible to grade and clearly show features of the swing till the impact by outputting level information of the plurality of items including the first item and the second item.

APPLICATION EXAMPLE 14

A swing diagnosis system according to this application example includes any one of the swing diagnosis apparatuses according to the application examples; and an inertial sensor that measures the swing.

The inertial sensor may be a sensor which can measure an inertial amount such as acceleration or angular velocity, and may be, for example, an inertial measurement unit (IMU) which can measure acceleration or angular velocity. For example, the inertial sensor may be attached to an exercise appliance or a part of a user so as to be attachable to and detachable from the exercise appliance or the user, and may be fixed to the exercise appliance so as to not be detached therefrom as a result of being built into the exercise appliance.

According to the swing diagnosis system of this application example, the swing diagnosis apparatus can level and diagnose a feature of the backswing or the downswing by calculating a level of the first item regarding at least one of the backswing and the downswing on the basis of the data regarding the swing, obtained through measurement in the inertial sensor. According to the swing diagnosis system of the application example, the swing diagnosis apparatus can also level and diagnose a feature of the swing at impact by calculating a level of the second item regarding the impact on the basis of the data regarding the swing, obtained through measurement in the inertial sensor. According to the swing diagnosis system of the application example, the swing diagnosis apparatus can level and clearly show features of the swing till the impact by outputting level information of the plurality of items including the first item and the second item.

BRIEF DESCRIPTION OF THE DRAWINGS

The invention will be described with reference to the accompanying drawings, wherein like numbers reference like elements.

FIG. 5 is a diagram illustrating an example of an input screen of physical information and golf club information.

FIG. 25 is a diagram illustrating an example of a rotation score table.

FIG. 26 is a diagram illustrating an example of an impact score table.

FIG. 27 is a diagram illustrating an example of a speed score table.

FIG. 28 is a diagram illustrating an example of a swing efficiency score table.

DESCRIPTION OF EXEMPLARY EMBODIMENTS

Hereinafter, preferred embodiments of the invention will be described with reference to the drawings. The embodiments described below are not intended to improperly limit the content of the invention disclosed in the appended claims. In addition, all constituent elements described below are not essential constituent elements of the invention.

Hereinafter, a swing diagnosis system performing diagnosis of a golf swing will be described as an example.

1. Swing Diagnosis System 1-1. Summary of Swing Diagnosis System

Figure 1:
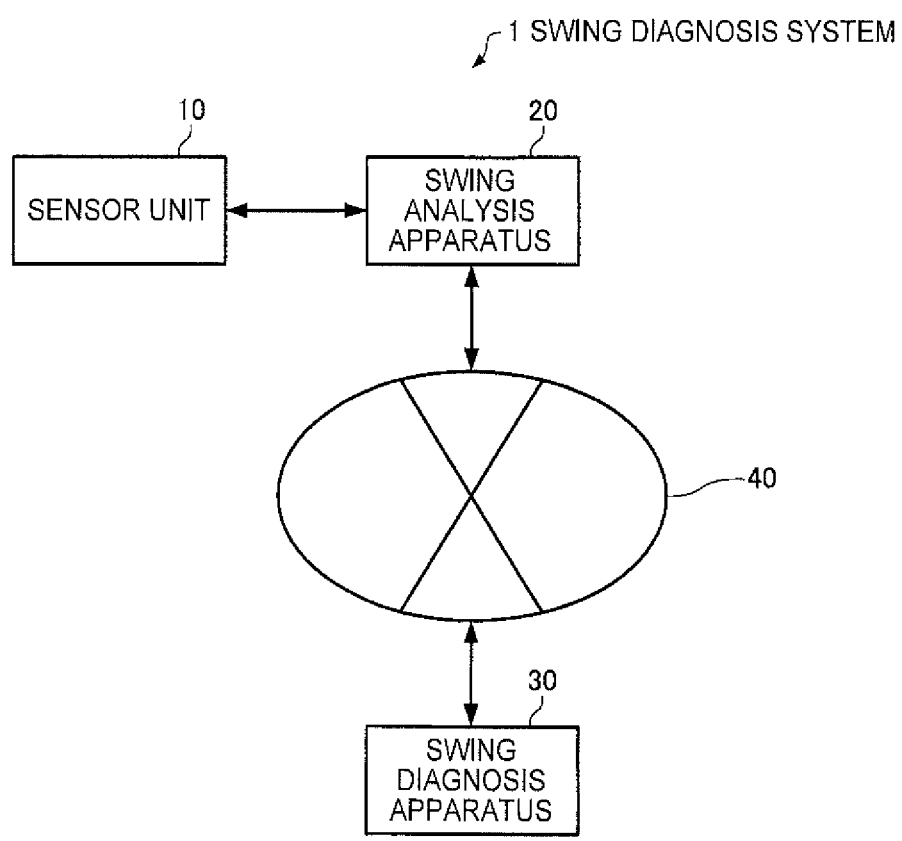
FIG. 1 is a diagram illustrating a configuration example of a swing diagnosis system of an embodiment.

FIG. 1 is a diagram illustrating a configuration example of a swing diagnosis system of the present embodiment. As illustrated in FIG. 1, a swing diagnosis system 1 of the present embodiment is configured to include a sensor unit 10, a swing analysis apparatus 20, and a swing diagnosis apparatus 30.

Figure 2:
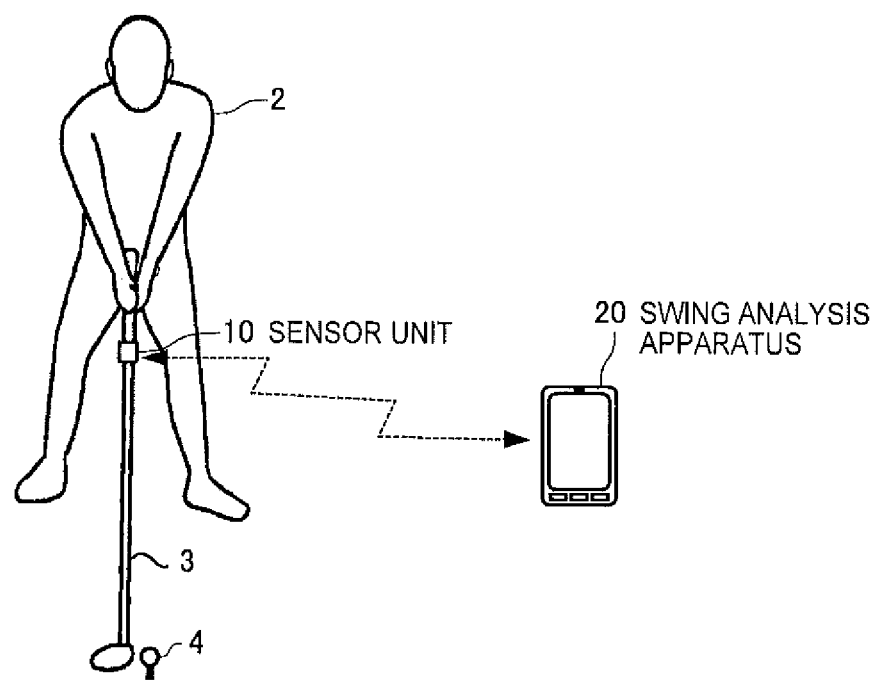
FIG. 2 is a diagram illustrating an example in which a sensor unit is attached.

The sensor unit 10 (an example of an inertial sensor measuring a swing) can measure acceleration generated in each axial direction of three axes and angular velocity generated around each of the three axes, and is attached to a golf club 3 as illustrated in FIG. 2.

Figure 3:
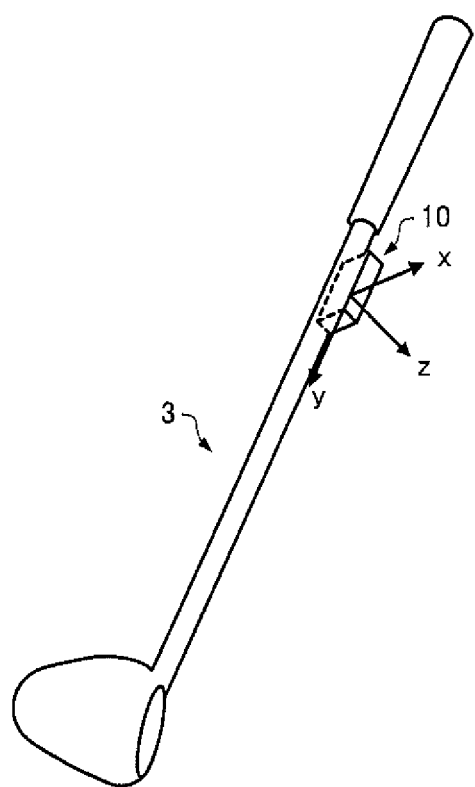
FIG. 3 is a diagram illustrating examples of a position at which and a direction in which the sensor unit is attached.

In the present embodiment, as illustrated in FIG. 3, the sensor unit 10 is attached to a part of a shaft so that one axis of three detection axes (an x axis, a y axis, and a z axis), for example, the y axis matches a longitudinal direction of the shaft of the golf club 3 (a longitudinal direction of the golf club 3). Preferably, the sensor unit 10 is attached to a position close to a grip to which impact during ball hitting is hardly forwarded and centrifugal force is hardly applied during swing. The shaft is a shaft portion other than a head of the golf club 3 and also includes the grip. However, the sensor unit 10 may be attached to a part (for example, the hand or a glove) of a user 2, and may be attached to an accessory such as a wristwatch.

Figure 4:
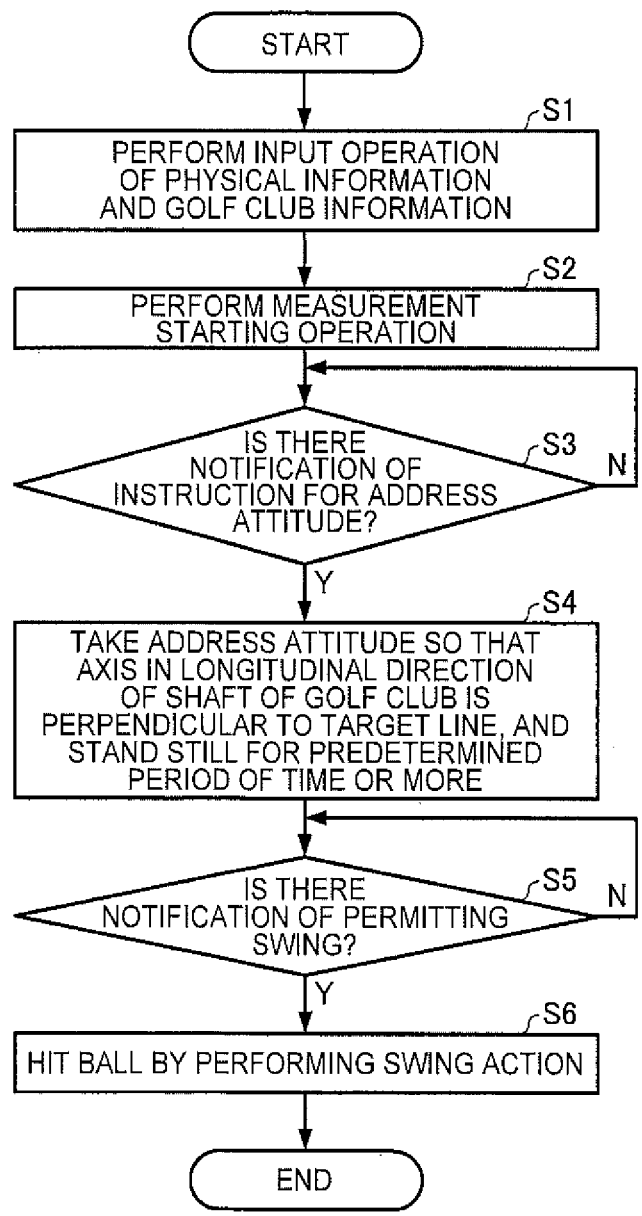
FIG. 4 is a diagram illustrating procedures of actions performed by a user until the user hits a ball.

The user 2 performs a swing action for hitting a golf ball 4 according to predefined procedures. FIG. 4 is a diagram illustrating procedures of actions performed by the user 2 until the user hits the ball in the present embodiment. As illustrated in FIG. 4, first, the user 2 performs an input operation of physical information of the user 2, information (golf club information) regarding the golf club 3 used by the user 2, and the like via the swing analysis apparatus 20 (step S1). The physical information includes at least one of information regarding a height, a length of the arms, and a length of the legs of the user 2, and may further include information regarding sex or other information. The golf club information includes at least one of information regarding a length (club length) of the golf club 3 and the type (number) of golf club 3. Next, the user 2 performs a measurement starting operation (an operation for starting measurement in the sensor unit 10) via the swing analysis apparatus 20 (step S2). Next, after receiving a notification (for example, a notification using a voice) of giving an instruction for taking an address attitude (a basic attitude before starting a swing) from the swing analysis apparatus 20 (Y in step S3), the user 2 takes an address attitude so that the axis in the longitudinal direction of the shaft of the golf club 3 is perpendicular to a target line (target hit ball direction), and stands still (step S4). Next, the user 2 receives a notification (for example, a notification using a voice) of permitting a swing from the swing analysis apparatus 20 (Y in step S5), and then hits the golf ball 4 by performing a swing action (step S6).

FIG. 5 is a diagram illustrating an example of an input screen of physical information and golf club information, displayed on a display section 25 (refer to FIG. 10) of the swing analysis apparatus 20. In step S1 in FIG. 4, the user 2 inputs physical information such as a height, sex, age, and country, and inputs golf club information such as a club length (a length of the shaft), and a club number on the input screen illustrated in FIG. 5. Information included in the physical information is not limited thereto, and, the physical information may include, for example, at least one of information regarding a length of the arms and a length of the legs instead of or along with the height. Similarly, information included in the golf club information is not limited thereto, and, for example, the golf club information may not include at least one of information regarding the club length and the number, and may include other information.

If the user 2 performs the measurement starting operation in step S2 in FIG. 4, the swing analysis apparatus 20 transmits a measurement starting command to the sensor unit 10, and the sensor unit 10 receives the measurement starting command and starts measurement of three-axis accelerations and three-axis angular velocities. The sensor unit 10 measures three-axis accelerations and three-axis angular velocities in a predetermined cycle (for example, 1 ms), and sequentially transmits the measured data to the swing analysis apparatus 20. Communication between the sensor unit 10 and the swing analysis apparatus 20 may be wireless communication, and may be wired communication.

The swing analysis apparatus 20 notifies the user 2 of permission of swing starting, shown in step S5 in FIG. 4, and then analyzes the swing action (step S6 in FIG. 4) in which the user 2 has hit the ball by using the golf club 3 on the basis of measured data from the sensor unit 10.

Figure 6:
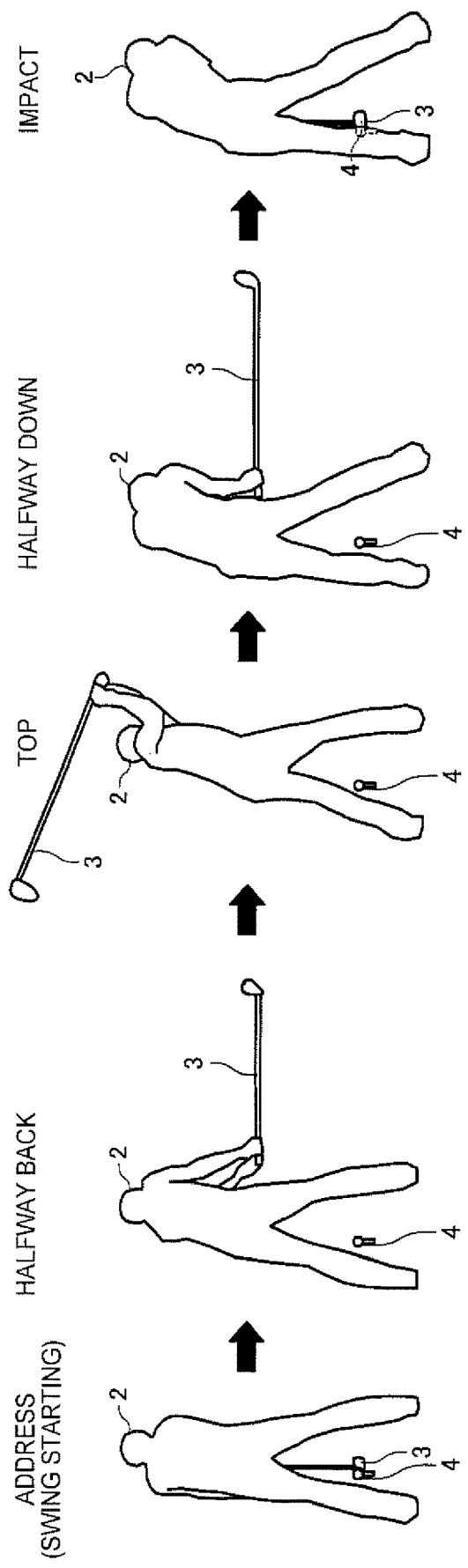
FIG. 6 is a diagram illustrating a swing action.

As illustrated in FIG. 6, the swing action performed by the user 2 in step S6 in FIG. 4 includes an action reaching impact (ball hitting) at which the golf ball 4 is hit through respective states of halfway back at which the shaft of the golf club 3 becomes horizontal during the backswing after starting a swing (backswing), a top at which the swing changes from the backswing to a downswing, and halfway down at which the shaft of the golf club 3 becomes horizontal during the downswing. The swing analysis apparatus 20 generates swing analysis data including information regarding a time point (date and time) at which the swing is performed, identification information or the sex of the user 2, the type of golf club 3, and an analysis result of the swing action, and transmits the swing analysis data to the swing diagnosis apparatus 30 via a network 40 (refer to FIG. 1).

The swing diagnosis apparatus 30 receives the swing analysis data transmitted by the swing analysis apparatus 20 via the network 40, and preserves the swing analysis data. Therefore, when the user 2 performs a swing action according to the procedures illustrated in FIG. 4, the swing analysis data generated by the swing analysis apparatus 20 is preserved in the swing diagnosis apparatus 30, and thus a swing analysis data list is built.

For example, the swing analysis apparatus 20 is implemented by an information terminal (client terminal) such as a smart phone or a personal computer, and the swing diagnosis apparatus 30 is implemented by a server which processes requests from the swing analysis apparatus 20.

The network 40 may be a wide area network (WAN) such as the Internet, and may be a local area network (LAN). The swing analysis apparatus 20 and the swing diagnosis apparatus 30 may communicate with each other through, for example, near field communication or wired communication, without using the network 40.

Figure 7:
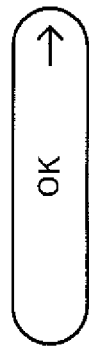
FIG. 7 is a diagram illustrating an example of a selection screen of swing analysis data.

In the present embodiment, if the user 2 activates a swing diagnosis application via an operation section 23 (refer to FIG. 10) of the swing analysis apparatus 20, the swing analysis apparatus 20 performs communication with the swing diagnosis apparatus 30, and, for example, a selection screen of swing analysis data as illustrated in FIG. 7 is displayed on the display section 25 of the swing analysis apparatus 20. The selection screen includes a time point (date and time), the type of golf club which has been used, and some index values as analysis results of a swing, with respect to each item of swing analysis data regarding the user 2 included in the swing analysis data list preserved in the swing diagnosis apparatus 30.

A checkbox correlated with each item of swing analysis data is located at a left end of the selection screen illustrated in FIG. 7, and the user 2 checks any one of the checkboxes by operating the swing analysis apparatus 20, and then presses an OK button located on a lower part of the selection screen. Consequently, the swing analysis apparatus 20 performs communication with the swing diagnosis apparatus 30, for example, an editing screen of input data which is a swing diagnosis target, as illustrated in FIG. 8, is displayed on the display section 25 of the swing analysis apparatus 20, with respect to the swing analysis data correlated with the checked checkbox on the selection screen illustrated in FIG. 7.

Figure 8:
FIG. 8 is a diagram illustrating an example of an editing screen of input data which is a swing diagnosis target.

The input data editing screen illustrated in FIG. 8 includes values obtained on the basis of the selected swing analysis data as initial values with respect to sex, the type of golf club (either of a driver or an iron), and each index of a swing. Meanings or calculation methods of the respective indexes (a region in which a head position at halfway back is included, a region in which a head position at halfway down is included, a face angle, a club path (incidence angle), a shaft axis rotation angle at top, a head speed, a grip deceleration ratio, and a grip deceleration time ratio) included in the input data editing screen illustrated in FIG. 8 will be described later.

The input data formed of the sex, the type of golf club, and the respective index values in the input data editing screen illustrated in FIG. 8 can be edited. The user 2 does not edit the input data or edits the input data via the operation section 23 (refer to FIG. 10) of the swing analysis apparatus 20, and then presses a diagnosis starting button located on a lower part of the input data editing screen. Consequently, the swing analysis apparatus 20 transmits the input data at the time of the diagnosis starting button being pressed to the swing diagnosis apparatus 30.

The swing diagnosis apparatus 30 receives the input data, and performs calculation of levels of a plurality of items by using the input data. For example, the swing diagnosis apparatus 30 may calculate a level of each of five items such as a "V zone", "rotation", "impact", a "speed", and "swing efficiency", as 5 points maximum. Meanings or calculation methods of the five items will be described later. The swing diagnosis apparatus 30 may calculate a total score of a swing by using the respective levels of the five items. The swing diagnosis apparatus 30 transmits information regarding the calculated levels and total score of the plurality of items to the swing analysis apparatus 20. The "levels" may be represented by, for example, "1, 2, 3, . . . ", "A, B, C, . . . ", "O, X, Δ, . . . ", and may be represented by scores.

Figure 9:
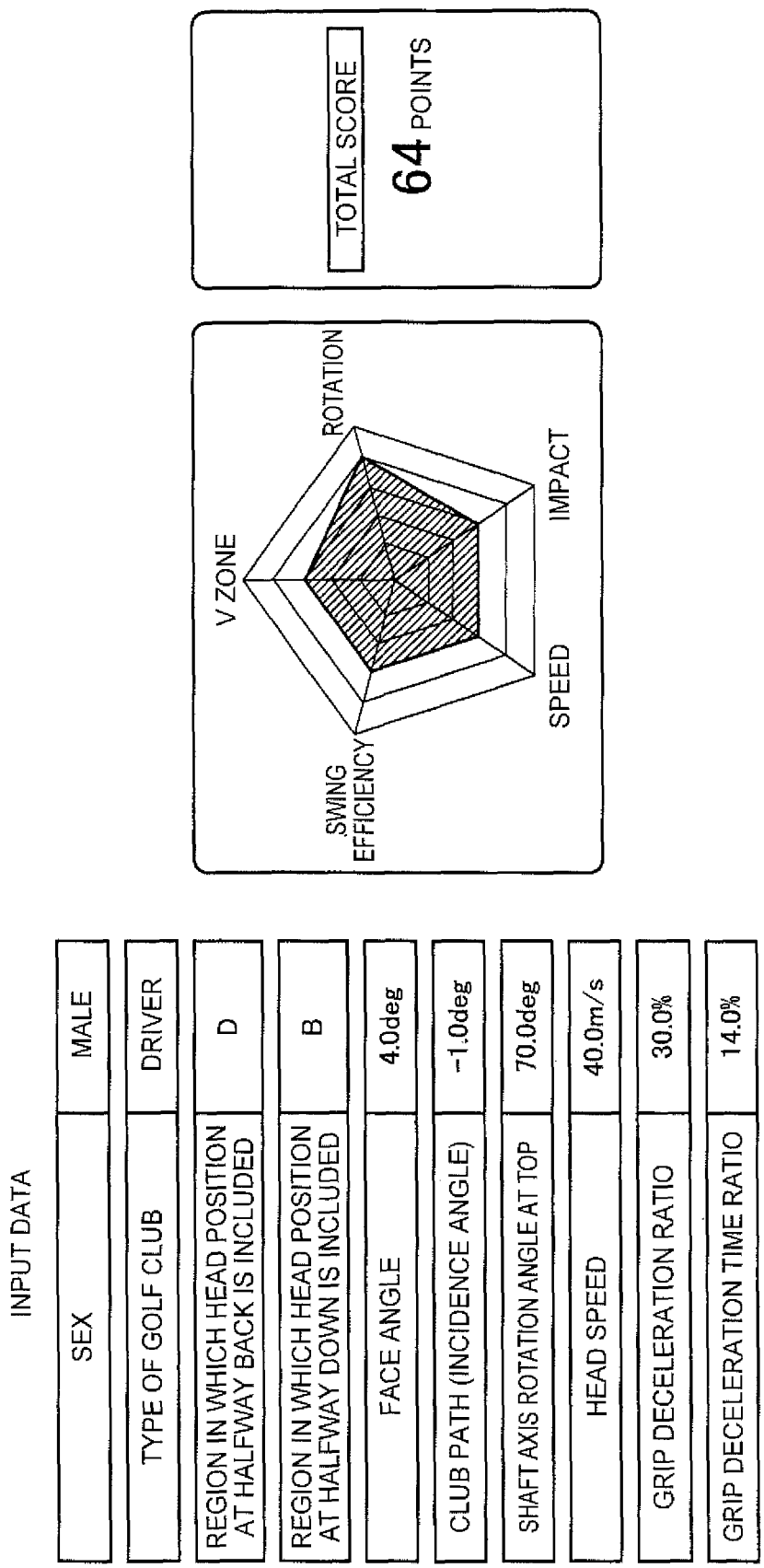
FIG. 9 is a diagram illustrating an example of a swing diagnosis screen.

The swing analysis apparatus 20 receives the information regarding levels and total score of the plurality of items, and displays, for example, a swing diagnosis screen as illustrated in FIG. 9 on the display section 25. The swing diagnosis screen illustrated in FIG. 9 includes input data information on a left part thereof. The input data information is input data at the time of the diagnosis starting button being pressed in the input data editing screen illustrated in FIG. 8, that is, data information used for diagnosis of the swing (that is, calculation of the levels and the total score of the five items) in the swing diagnosis apparatus 30. The swing diagnosis screen illustrated in FIG. 9 includes a radar chart indicating scores as the levels of the five items on the central part thereof, and includes information regarding the total score on a right part thereof.

The user 2 can understand levels and a total score of the plurality of items as diagnosis results for the input data on the left part on the basis of the swing diagnosis screen illustrated in FIG. 9. Particularly, if the user 2 presses the diagnosis starting button without editing the input data on the input data editing screen illustrated in FIG. 8, the user can understand a strong point or a weak point in the user's swing on the basis of the swing diagnosis screen illustrated in FIG. 9. On the other hand, if the user 2 edits the input data and presses the diagnosis starting button on the input data editing screen illustrated in FIG. 8, the user can understand which index is improved to what extent in order to overcome the weak point. Hereinafter, a description will be made of an example in which "levels" of a plurality of items are represented by "scores", but, needless to say, the example can be easily replaced with an example of the levels being expressed by "1, 2, 3, . . . ", "A, B, C, . . . ", "O, X, Δ", or the like.

1-2. Configuration of Sensor Unit and Swing Analysis Apparatus

Figure 10:
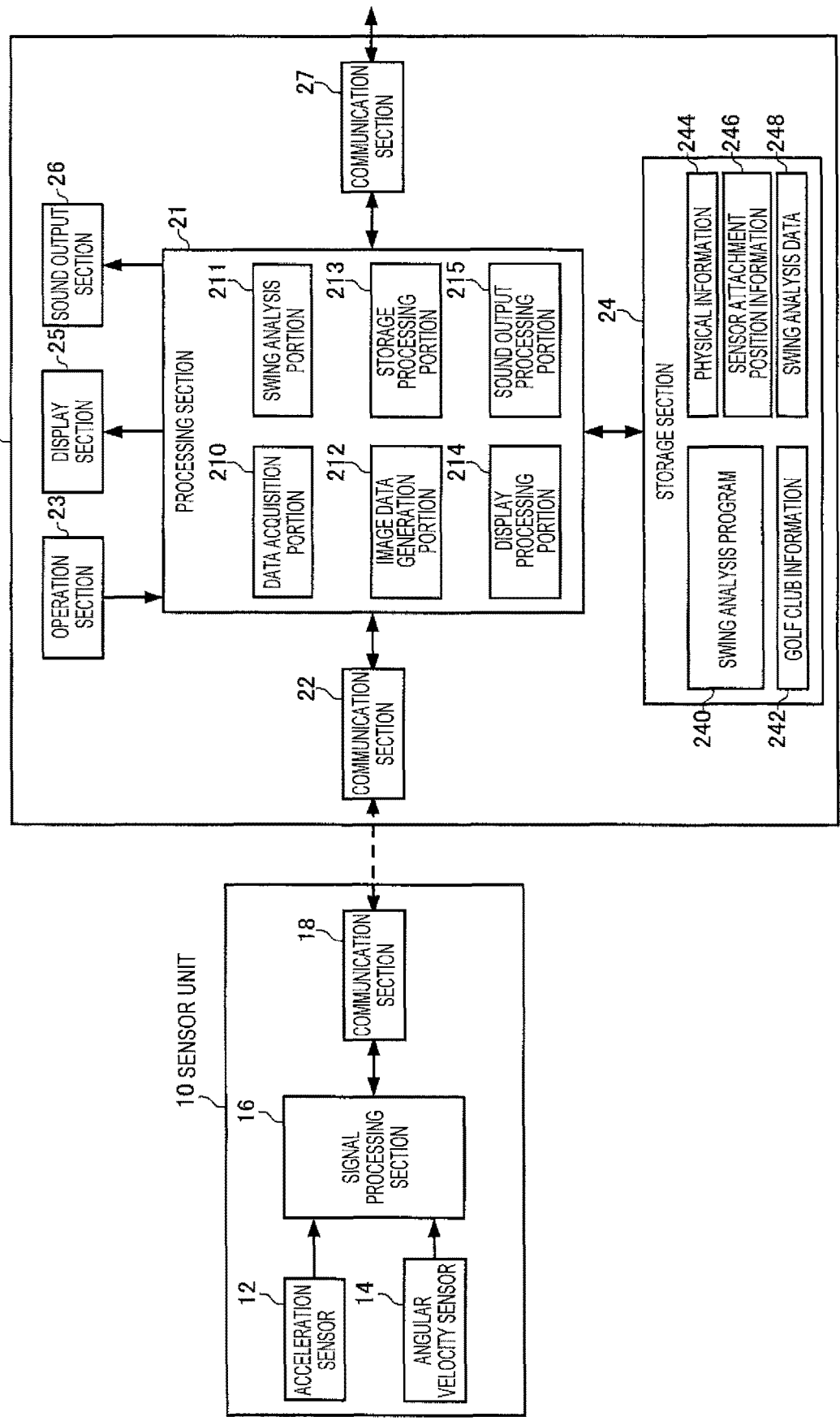
FIG. 10 is a diagram illustrating configuration examples of the sensor unit and a swing analysis apparatus.

FIG. 10 is a diagram illustrating configuration examples of the sensor unit 10 and the swing analysis apparatus 20. As illustrated in FIG. 10, in the present embodiment, the sensor unit 10 is configured to include an acceleration sensor 12, an angular velocity sensor 14, a signal processing section 16, and a communication section 18. However, the sensor unit 10 may have a configuration in which some of the constituent elements are deleted or changed as appropriate, or may have a configuration in which other constituent elements are added thereto.

The acceleration sensor 12 measures respective accelerations in three axial directions which intersect (ideally, orthogonal to) each other, and outputs digital signals (acceleration data) corresponding to magnitudes and directions of the measured three-axis accelerations.

The angular velocity sensor 14 measures respective angular velocities in three axial directions which intersect (ideally, orthogonal to) each other, and outputs digital signals (angular velocity data) corresponding to magnitudes and directions of the measured three-axis angular velocities.

The signal processing section 16 receives the acceleration data and the angular velocity data from the acceleration sensor 12 and the angular velocity sensor 14, respectively, adds time information thereto, stores the data in a storage portion (not illustrated), adds time information to the stored measured data (acceleration data and angular velocity data) so as to generate packet data conforming to a communication format, and outputs the packet data to the communication section 18.

Ideally, the acceleration sensor 12 and the angular velocity sensor 14 are provided in the sensor unit 10 so that the three axes thereof match three axes (an x axis, a y axis, and a z axis) of an orthogonal coordinate system (sensor coordinate system) defined for the sensor unit 10, but, actually, errors occur in installation angles. Therefore, the signal processing section 16 performs a process of converting the acceleration data and the angular velocity data into data in the xyz coordinate system by using a correction parameter which is calculated in advance according to the installation angle errors.

The signal processing section 16 may perform a process of correcting the temperatures of the acceleration sensor 12 and the angular velocity sensor 14. The acceleration sensor 12 and the angular velocity sensor 14 may have a temperature correction function.

The acceleration sensor 12 and the angular velocity sensor 14 may output analog signals, and, in this case, the signal processing section 16 may A/D convert an output signal from the acceleration sensor 12 and an output signal from the angular velocity sensor 14 so as to generate measured data (acceleration data and angular velocity data), and may generate communication packet data by using the data.

The communication section 18 performs a process of transmitting packet data received from the signal processing section 16 to the swing analysis apparatus 20, or a process of receiving various control commands such as a measurement starting command from the swing analysis apparatus 20 and sending the control command to the signal processing section 16. The signal processing section 16 performs various processes corresponding to control commands.

As illustrated in FIG. 10, in the present embodiment, the swing analysis apparatus 20 is configured to include a processing section 21, a communication section 22, an operation section 23, a storage section 24, a display section 25, a sound output section 26, and a communication section 27. However, the swing analysis apparatus 20 may have a configuration in which some of the constituent elements are deleted or changed as appropriate, or may have a configuration in which other constituent elements are added thereto.

The communication section 22 performs a process of receiving packet data transmitted from the sensor unit 10 and sending the packet data to the processing section 21, or a process of transmitting a control command from the processing section 21 to the sensor unit 10.

The operation section 23 performs a process of acquiring operation data from the user 2 and sending the operation data to the processing section 21. The operation section 23 may be, for example, a touch panel type display, a button, a key, or a microphone.

The storage section 24 is constituted of, for example, various IC memories such as a read only memory (ROM), a flash ROM, and a random access memory (RAM), or a recording medium such as a hard disk or a memory card. The storage section 24 stores a program for the processing section 21 performing various calculation processes or a control process, or various programs or data for realizing application functions.

In the present embodiment, the storage section 24 stores a swing analysis program 240 which is read by the processing section 21 and executes a swing analysis process. The swing analysis program 240 may be stored in a nonvolatile recording medium (computer readable recording medium) in advance, or the swing analysis program 240 may be received from a server (not illustrated) or the swing diagnosis apparatus 30 by the processing section 21 via a network, and may be stored in the storage section 24.

In the present embodiment, the storage section 24 stores golf club information 242, physical information 244, sensor attachment position information 246, and swing analysis data 248. For example, the user 2 may operate the operation section 23 so as to input specification information regarding the golf club 3 to be used (for example, at least some information such as information regarding a length of the shaft, a position of the centroid thereof, a lie angle, a face angle, a loft angle, and the like) from the input screen illustrated in FIG. 5, and the input specification information may be used as the golf club information 242. Alternatively, in step S1 in FIG. 4, the user 2 may sequentially input type numbers of the golf club 3 (alternatively, selects a type number from a type number list) so that specification information for each type number is stored in the storage section 24 in advance. In this case, specification information of an input type number may be used as the golf club information 242.

For example, the user 2 may input physical information by operating the operation section 23 from the input screen illustrated in FIG. 5, and the input physical information may be used as the physical information 244. For example, in step S1 in FIG. 4, the user 2 may input an attachment position of the sensor unit 10 and a distance to the grip end of the golf club 3 by operating the operation section 23, and the input distance information may be used as the sensor attachment position information 246. Alternatively, the sensor unit 10 may be attached at a defined predetermined position (for example, a distance of 20 cm from the grip end), and thus information regarding the predetermined position may be stored as the sensor attachment position information 246 in advance.

The swing analysis data 248 is data including information regarding a swing action analysis result in the processing section 21 (swing analysis portion 211) along with a time point (date and time) at which a swing was performed, identification information or the sex of the user 2, and the type of golf club 3.

The storage section 24 is used as a work area of the processing section 21, and temporarily stores data which is input from the operation section 23, results of calculation executed by the processing section 21 according to various programs, and the like. The storage section 24 may store data which is required to be preserved for a long period of time among data items generated through processing of the processing section 21.

The display section 25 displays a processing result in the processing section 21 as text, a graph, a table, animation, and other images. The display section 25 may be, for example, a CRT, an LCD, a touch panel type display, and a head mounted display (HMD). A single touch panel type display may realize functions of the operation section 23 and the display section 25.

The sound output section 26 outputs a processing result in the processing section 21 as a sound such as a voice or a buzzer sound. The sound output section 26 may be, for example, a speaker or a buzzer.

The communication section 27 performs data communication with a communication section 32 (refer to FIG. 22) of the swing diagnosis apparatus 30 via the network 40. For example, the communication section 27 performs a process of receiving the swing analysis data 248 from the processing section 21 after a swing analysis process is completed, and transmitting the swing analysis data to the communication section 32 of the swing diagnosis apparatus 30. For example, the communication section 27 performs a process of receiving information required to display the selection screen illustrated in FIG. 7 from the communication section 32 of the swing diagnosis apparatus 30 and transmitting the information to the processing section 21, and a process of receiving selected information on the selection screen illustrated in FIG. 7 from the processing section 21 and transmitting the selected information to the communication section 32 of the swing diagnosis apparatus 30. For example, the communication section 27 performs a process of receiving information required to display the input data editing screen illustrated in FIG. 8 from the communication section 32 of the swing diagnosis apparatus 30, and transmitting the information to the processing section 21. For example, the communication section 27 performs a process of receiving input data at the time of the diagnosis starting button on the input data editing screen illustrated in FIG. 8 being pressed from the processing section 21, and transmitting the input data to the communication section 32 of the swing diagnosis apparatus 30. For example, the communication section 27 performs a process of receiving information (diagnosis result information (scores or a total score of a plurality of items) based on the input data) required to display the swing diagnosis screen illustrated in FIG. 9 from the communication section 32 of the swing diagnosis apparatus 30, and transmitting the information to the processing section 21.

The processing section 21 performs a process of transmitting a control command to the sensor unit 10 via the communication section 22, or various computation processes on data which is received from the sensor unit 10 via the communication section 22, according to various programs. The processing section 21 performs a process of reading the swing analysis data 248 from the storage section 24, and transmitting the swing analysis data to the swing diagnosis apparatus 30 via the communication section 27, according to various programs. The processing section 21 performs a process of transmitting various pieces of information to the swing diagnosis apparatus 30 via the communication section 27, and displaying various screens (the respective screens illustrated in FIGS. 7, 8 and 9) on the basis of the information received from the swing diagnosis apparatus 30, according to various programs. The processing section 21 performs other various control processes.

Particularly, in the present embodiment, by executing the swing analysis program 240, the processing section 21 functions as a data acquisition portion 210, a swing analysis portion 211, an image data generation portion 212, a storage processing portion 213, a display processing portion 214, and a sound output processing portion 215, and performs a process (swing analysis process) of analyzing a swing action of the user 2.

The data acquisition portion 210 performs a process of receiving packet data which is received from the sensor unit 10 by the communication section 22, acquiring time information and measured data in the sensor unit 10 from the received packet data, and sending the time information and the measured data to the storage processing portion 213. The data acquisition portion 210 performs a process of receiving the information required to display the various screens (the respective screens illustrated in FIGS. 7, 8 and 9), received from the swing diagnosis apparatus 30 by the communication section 27, and transmitting the information to the image data generation portion 212.

The storage processing portion 213 performs read/write processes of various programs or various data for the storage section 24. The storage processing portion 213 performs not only the process of storing the time information and the measured data received from the data acquisition portion 210 in the storage section 24 in correlation with each other, but also a process of storing various pieces of information calculated by the swing analysis portion 211, the swing analysis data 248, or the like in the storage section 24.

The swing analysis portion 211 performs a process of analyzing a swing action of the user 2 by using the measured data (the measured data stored in the storage section 24) output from the sensor unit 10, the data from the operation section 23, or the like, so as to generate the swing analysis data 248 including a time point (date and time) at which the swing was performed, identification information or the sex of the user 2, the type of golf club 3, and information regarding a swing action analysis result. Particularly, in the present embodiment, the swing analysis portion 211 calculates a value of each index of the swing as at least some of the information regarding the swing action analysis result.

The swing analysis portion 211 may calculate at least one virtual plane as an index of the swing. For example, at least one virtual plane includes a shaft plane SP (first virtual plane) which will be described later, and a Hogan plane HP (second virtual plane) which will be described later forming a first angle with the shaft plane SP, and the swing analysis portion 211 may calculate the "shaft plane SP" and the "Hogan plane HP" as the indexes.

The swing analysis portion 211 may calculate a position of the head of the golf club 3 at a first timing during the backswing as an index of the swing. For example, the first timing is the time of halfway back at which the longitudinal direction of the golf club 3 becomes a direction along the horizontal direction during the backswing, and the swing analysis portion 211 may calculate a "position of the head at halfway back" which will be described later as the index.

The swing analysis portion 211 may calculate a position of the head of the golf club 3 at a second timing during the downswing as an index of the swing. For example, the second timing is the time of halfway down at which the longitudinal direction of the golf club 3 becomes a direction along the horizontal direction during the downswing, and the swing analysis portion 211 may calculate a "position of the head at halfway down" which will be described later as the index.

The swing analysis portion 211 may calculate an index based on an incidence angle of the head of the golf club 3 at impact (at ball hitting), as an index of the swing. For example, the swing analysis portion 211 may calculate a "club path (incidence angle) $\psi$" which will be described later as the index.

The swing analysis portion 211 may calculate an index based on an inclination of the head of the golf club 3 at impact (at ball hitting) as an index of the swing. For example, the swing analysis portion 211 may calculate an "(absolute) face angle $\phi$" or a "relative face angle $\eta$" which will be described later as the index.

The swing analysis portion 211 may calculate an index based on a speed of the head of the golf club 3 at impact (at ball hitting) as an index of the swing. For example, the swing analysis portion 211 may calculate a "head speed" which will be described later as the index.

The swing analysis portion 211 may calculate an index based on a rotation angle about a rotation axis (hereinafter, referred to as about the long axis) of the shaft of the golf club 3 at a predetermined timing between the time of starting a backswing and the time of impact (at ball hitting) with the longitudinal direction of the shaft as the rotation axis, as an index of the swing. The rotation angle about the long axis of the golf club 3 may be an angle by which the golf club 3 is rotated about the long axis from a reference timing to a predetermined timing. The reference timing may be the time of starting a backswing, and may be the time of address. The predetermined timing may be the time (the time of a top) at which a backswing transitions to a downswing. For example, the swing analysis portion 211 may calculate a "shaft axis rotation angle $\theta_{top}$ at top" which will be described later as the index.

The swing analysis portion 211 may calculate an index based on a deceleration amount of the grip of the golf club 3 during the downswing as an index of the swing. For example, the swing analysis portion 211 may calculate a "grip deceleration ratio $R_V$" which will be described later as the index.

The swing analysis portion 211 may calculate an index based on a deceleration period of the grip of the golf club 3 during the downswing as an index of the swing. For example, the swing analysis portion 211 may calculate a "grip deceleration time ratio $R_T$" which will be described later as the index.

However, the swing analysis portion 211 may not calculate values of some of the indexes, and may calculate values of other indexes, as appropriate.

The image data generation portion 212 performs a process of generating image data corresponding to an image displayed on the display section 25. For example, the image data generation portion 212 generates image data corresponding to the selection screen illustrated in FIG. 7, the input data editing screen illustrated in FIG. 8, and the swing diagnosis screen illustrated in FIG. 9 on the basis of various pieces of information received by the data acquisition portion 210.

The display processing portion 214 performs a process of displaying various images (including text, symbols, and the like in addition to an image corresponding to the image data generated by the image data generation portion 212) on the display section 25. For example, the display processing portion 214 displays the selection screen illustrated in FIG. 7, the input data editing screen illustrated in FIG. 8, the swing diagnosis screen illustrated in FIG. 9, and the like, on the display section 25, on the basis of the image data generated by the image data generation portion 212. For example, the image data generation portion 212 may display an image, text, or the like for notifying the user 2 of permission of swing starting on the display section 25 in step S5 in FIG. 4. For example, the display processing portion 214 may display text information such as text or symbols indicating an analysis result in the swing analysis portion 211 on the display section 25 automatically or in response to an input operation performed by the user 2 after a swing action of the user 2 is completed. Alternatively, a display section may be provided in the sensor unit 10, and the display processing portion 214 may transmit image data to the sensor unit 10 via the communication section 22, and various images, text, or the like may be displayed on the display section of the sensor unit 10.

The sound output processing portion 215 performs a process of outputting various sounds (including voices, buzzer sounds, and the like) from the sound output section 26. For example, the sound output processing portion 215 may output a sound for notifying the user 2 of permission of swing starting from the sound output section 26 in step S5 in FIG. 4. For example, the sound output processing portion 215 may output a sound or a voice indicating an analysis result in the swing analysis portion 211 from the sound output section 26 automatically or in response to an input operation performed by the user 2 after a swing action of the user 2 is completed. Alternatively, a sound output section may be provided in the sensor unit 10, and the sound output processing portion 215 may transmit various items of sound data or voice data to the sensor unit 10 via the communication section 22, and may output various sounds or voices from the sound output section of the sensor unit 10.

A vibration mechanism may be provided in the swing analysis apparatus 20 or the sensor unit 10, and various pieces of information may be converted into vibration information by the vibration mechanism so as to be presented to the user 2.

1-3. Swing Analysis Process

In the present embodiment, when a position of the head of the golf club 3 at address (during standing still) is set to the origin, an XYZ coordinate system (global coordinate system) is defined which has a target line indicating a target hit ball direction as an X axis, an axis on a horizontal plane which is perpendicular to the X axis as a Y axis, and a vertically upward direction (a direction opposite to the gravitational direction) as a Z axis. In order to calculate each index value, the swing analysis portion 211 calculates a position and an attitude of the sensor unit 10 in a time series from the time of the address in the XYZ coordinate system (global coordinate system) by using measured data (acceleration data and angular velocity data) in the sensor unit 10. The swing analysis portion 211 detects respective timings of the swing starting, the top, and the impact illustrated in FIG. 6, by using the measured data (acceleration data or angular velocity data) in the sensor unit 10. The swing analysis portion 211 calculates values of the respective indexes (for example, a shaft plane, a Hogan plane, a head position at halfway back, a head position at halfway down, a face angle, a club path (incidence angle), a shaft axis rotation angle at top, a head speed, a grip deceleration ratio, and a grip deceleration time ratio) of the swing by using the time series data of the position and the attitude of the sensor unit 10, and the timings of the swing starting, the top, and the impact, so as to generate the swing analysis data 248.

Calculation of Position and Attitude of Sensor Unit 10

If the user 2 performs the action in step S4 in FIG. 4, first, the swing analysis portion 211 determines that the user 2 stands still at an address attitude in a case where an amount of changes in acceleration data measured by the acceleration sensor 12 does not continuously exceed a threshold value for a predetermined period of time. Next, the swing analysis portion 211 computes an offset amount included in the measured data by using the measured data (acceleration data and angular velocity data) for the predetermined period of time. Next, the swing analysis portion 211 subtracts the offset amount from the measured data so as to perform bias correction, and computes a position and an attitude of the sensor unit 10 during a swing action of the user 2 (during the action in step S6 in FIG. 4) by using the bias-corrected measured data.

Specifically, first, the swing analysis portion 211 computes a position (initial position) of the sensor unit 10 during standing still (at address) of the user 2 in the XYZ coordinate system (global coordinate system) by using the acceleration data measured by the acceleration sensor 12, the golf club information 242, and the sensor attachment position information 246.

Figure 11:
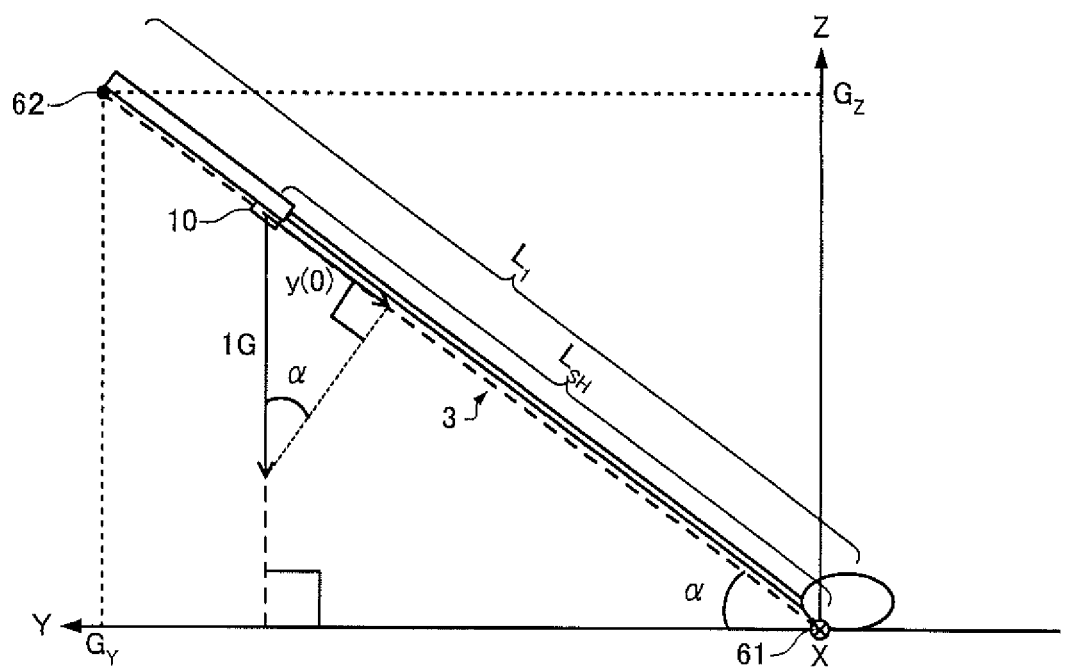
FIG. 11 is a plan view in which a golf club and the sensor unit are viewed from a negative side of an X axis during standing still of the user.

FIG. 11 is a plan view in which the golf club 3 and the sensor unit 10 during standing still (at address) of the user 2 are viewed from a negative side of the X axis. The origin O (0,0,0) is set at a position 61 of the head of the golf club 3, and coordinates of a position 62 of a grip end are (0, $G_Y$, $G_Z$). Since the user 2 performs the action in step S4 in FIG. 4, the position 62 of the grip end or the initial position of the sensor unit 10 has an X coordinate of 0, and is present on a YZ plane. As illustrated in FIG. 11, the gravitational acceleration of 1 G is applied to the sensor unit 10 during standing still of the user 2, and thus a relationship between a y axis acceleration y (0) measured by the sensor unit 10 and an inclined angle (an angle formed between the long axis of the shaft and the horizontal plane (XY plane)) α of the shaft of the golf club 3 is expressed by Equation (1).

$$y(0)=1G \cdot \sin \alpha \quad (1)$$

Therefore, the swing analysis portion 211 can calculate the inclined angle α according to Equation (1) by using any acceleration data between any time points at address (during standing still).

Next, the swing analysis portion 211 subtracts a distance $L_{SG}$ between the sensor unit 10 and the grip end included in the sensor attachment position information 246 from a length $L_1$ of the shaft included in the golf club information 242, so as to obtain a distance $L_{SH}$ between the sensor unit 10 and the head. The swing analysis portion 211 sets, as the initial position of the sensor unit 10, a position separated by the distance $L_{SH}$ from the position 61 (origin O) of the head in a direction (a negative direction of the y axis of the sensor unit 10) specified by the inclined angle α of the shaft.

The swing analysis portion 211 integrates subsequent acceleration data so as to compute coordinates of a position from the initial position of the sensor unit 10 in a time series.

The swing analysis portion 211 computes an attitude (initial attitude) of the sensor unit 10 during standing still (at address) of the user 2 in the XYZ coordinate system (global coordinate system) by using acceleration data measured by the acceleration sensor 12. Since the user 2 performs the action in step S4 in FIG. 4, the x axis of the sensor unit 10 matches the X axis of the XYZ coordinate system in terms of direction at address (during standing still) of the user 2, and the y axis of the sensor unit 10 is present on the YZ plane. Therefore, the swing analysis portion 211 can specify the initial attitude of the sensor unit 10 on the basis of the inclined angle α of the shaft of the golf club 3.

The swing analysis portion 211 computes changes in attitudes from the initial attitude of the sensor unit 10 in time series by performing rotation calculation using angular velocity data which is subsequently measured by the angular velocity sensor 14. An attitude of the sensor unit 10 may be expressed by, for example, rotation angles (a roll angle, a pitch angle, and a yaw angle) about the X axis, the Y axis, and the Z axis, or a quaternion.

The signal processing section 16 of the sensor unit 10 may compute an offset amount of measured data so as to perform bias correction on the measured data, and the acceleration sensor 12 and the angular velocity sensor 14 may have a bias correction function. In this case, it is not necessary for the swing analysis portion 211 to perform bias correction on the measured data.

Detection of Swing Starting, Top and Impact Timings

First, the swing analysis portion 211 detects a timing (impact timing) at which the user 2 hit a ball by using measured data. For example, the swing analysis portion 211 may compute a combined value of measured data (acceleration data or angular velocity data), and may detect an impact timing (time point) on the basis of the combined value.

Specifically, first, the swing analysis portion 211 computes a combined value $n_0(t)$ of angular velocities at each time point t by using the angular velocity data (bias-corrected angular velocity data for each time point t). For example, if the angular velocity data items at the time point t are respectively indicated by x(t), y(t), and z(t), the swing analysis portion 211 computes the combined value $n_0(t)$ of the angular velocities according to the following Equation (2).

$$n_0(t) = \sqrt{x(t)^2 + y(t)^2 + z(t)^2} \quad (2)$$

Next, the swing analysis portion 211 converts the combined value $n_0(t)$ of the angular velocities at each time point t into a combined value n(t) which is normalized (scale-conversion) within a predetermined range. For example, if the maximum value of the combined value of the angular velocities in an acquisition period of measured data is max ($n_0$), the swing analysis portion 211 converts the combined value $n_0(t)$ of the angular velocities into the combined value n(t) which is normalized within a range of 0 to 100 according to the following Equation (3).

$$n(t) = \frac{100 \times n_0(t)}{\max(n_0)} \quad (3)$$

Next, the swing analysis portion 211 computes a derivative dn(t) of the normalized combined value n(t) at each time point t. For example, if a cycle for measuring three-axis angular velocity data items is indicated by $\Delta t$, the swing analysis portion 211 computes the derivative (difference) dn(t) of the combined value of the angular velocities at the time point t by using the following Equation (4).

$$dn(t) = n(t) - n(t - \Delta t) \quad (4)$$

Figure 12:
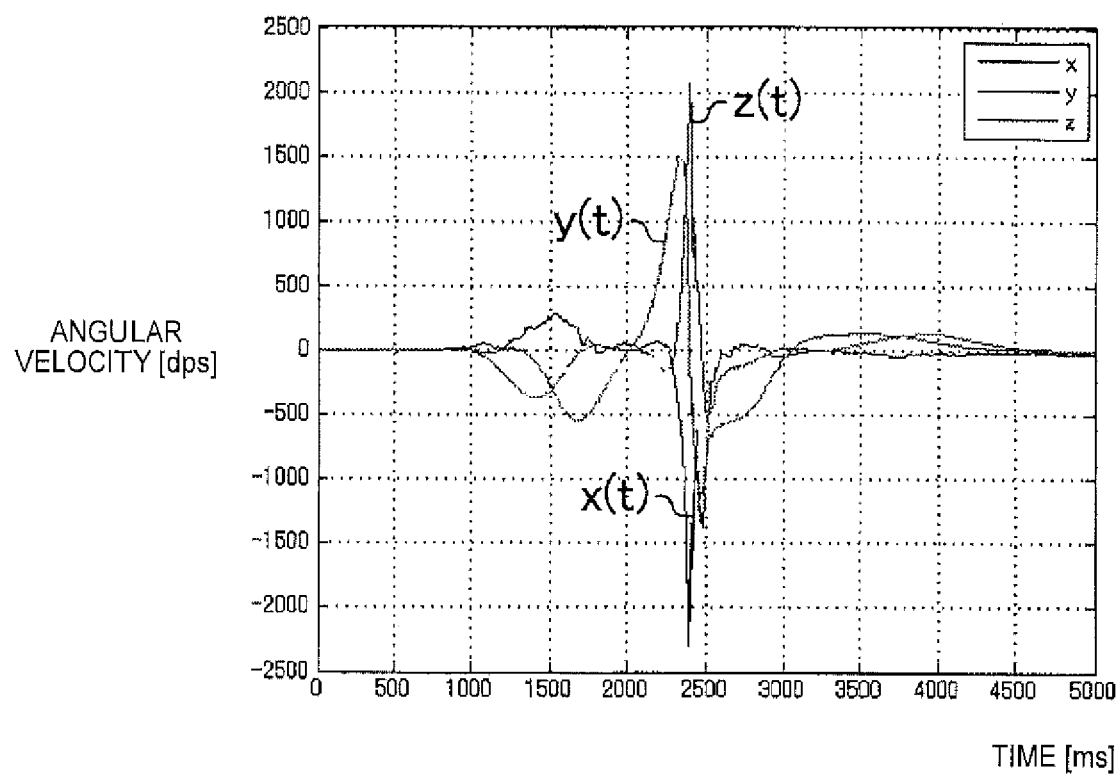
FIG. 12 is a graph illustrating examples of temporal changes of three-axis angular velocities.

FIG. 12 illustrates examples of three-axis angular velocity data items x(t), y(t) and z(t) obtained when the user 2 hits the golf ball 4 by performing a swing. In FIG. 12, a transverse axis expresses time (msec), and a longitudinal axis expresses angular velocity (dps).

Figure 13:
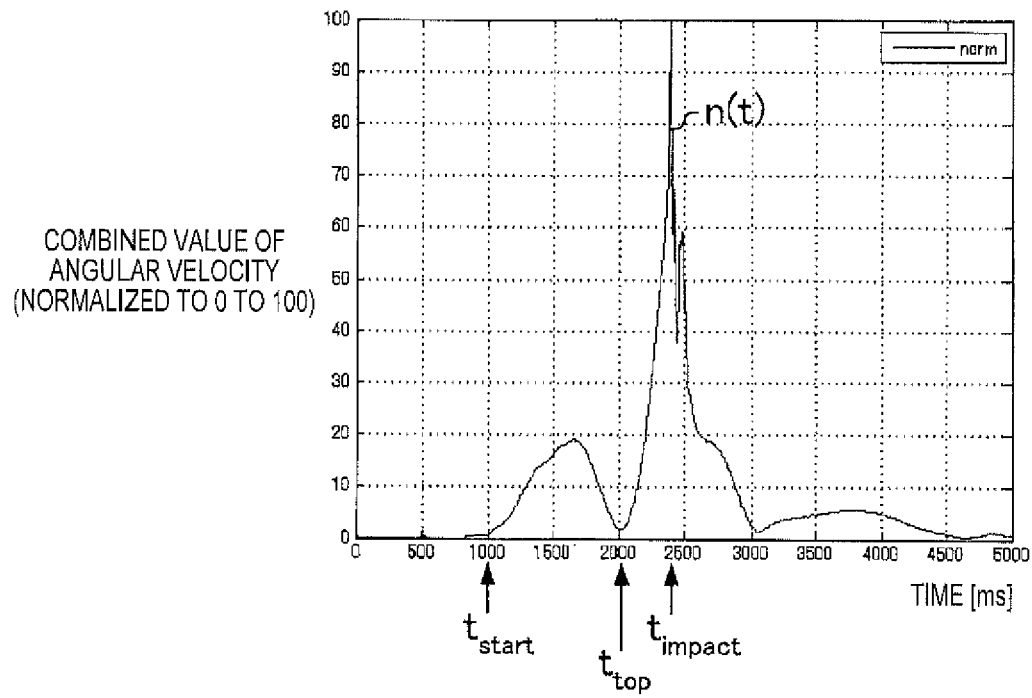
FIG. 13 is a graph illustrating a temporal change of a combined value of the three-axis angular velocities.

FIG. 13 is a diagram in which the combined value no (t) of the three-axis angular velocities is computed according to Equation (2) by using the three-axis angular velocity data items x(t), y(t) and z(t) in FIG. 12, and then the combined value n(t) normalized to 0 to 100 according to Equation (3) is displayed in a graph. In FIG. 13, a transverse axis expresses time (msec), and a longitudinal axis expresses a combined value of the angular velocity.

Figure 14:
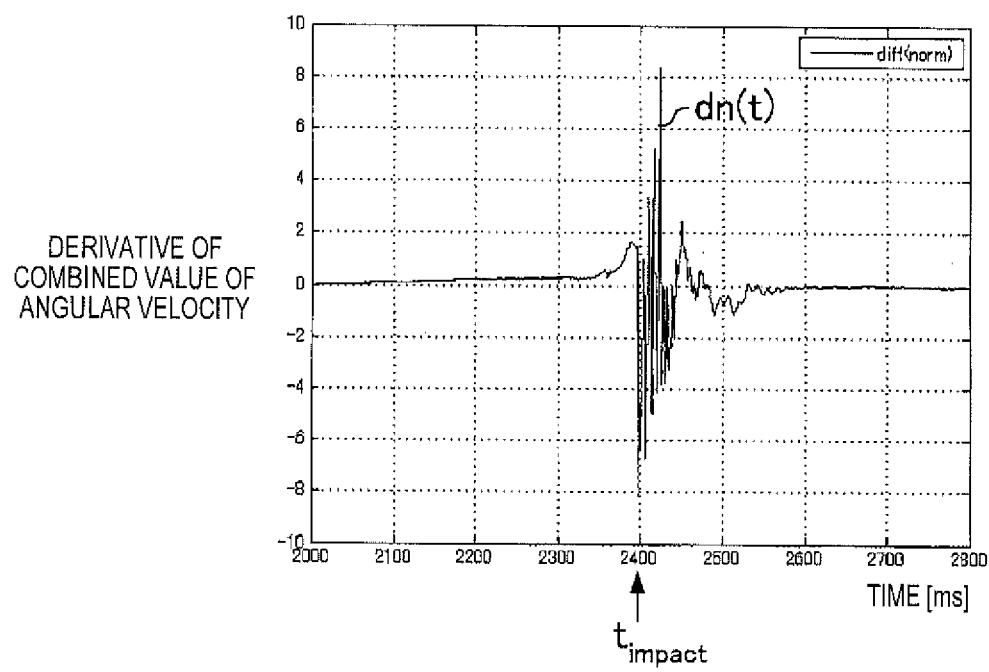
FIG. 14 is a graph illustrating a temporal change of a derivative of the combined value.

FIG. 14 is a diagram in which the derivative dn(t) is calculated according to Equation (4) on the basis of the combined value n(t) of the three-axis angular velocities in FIG. 13, and is displayed in a graph. In FIG. 14, a transverse axis expresses time (msec), and a longitudinal axis expresses a derivative value of the combined value of the three-axis angular velocities. In FIGS. 12 and 13, the transverse axis is displayed at 0 seconds to 5 seconds, but, in FIG. 14, the transverse axis is displayed at 2 seconds to 2.8 seconds so that changes in the derivative value before and after impact can be understood.

Next, of time points at which a value of the derivative dn(t) of the combined value becomes the maximum and the minimum, the swing analysis portion 211 detects the earlier time point as an impact time point $t_{impact}$ (impact timing) (refer to FIG. 14). It is considered that swing speed is the maximum at the moment of impact in a typical golf swing. In addition, since it is considered that a value of the combined value of the angular velocities also changes according to a swing speed, the swing analysis portion 211 can capture a timing at which a derivative value of the combined value of the angular velocities is the maximum or the minimum (that is, a timing at which the derivative value of the combined value of the angular velocities is a positive maximum value or a negative minimum value) in a series of swing actions as the impact timing. Since the golf club 3 vibrates due to the impact, a timing at which a derivative value of the combined value of the angular velocities is the maximum and a timing at which a derivative value of the combined value of the angular velocities is the minimum may occur in pairs, and, of the two timings, the earlier timing may be the moment of the impact.

Next, the swing analysis portion 211 detects a time point of a minimum point at which the combined value n(t) is close to 0 before the impact time point $t_{impact}$, as a top time point $t_{top}$ (top timing) (refer to FIG. 13). It is considered that, in a typical golf swing, an action temporarily stops at the top after starting the swing, then a swing speed increases, and finally impact occurs. Therefore, the swing analysis portion 211 can capture a timing at which the combined value of the angular velocities is close to 0 and becomes the minimum before the impact timing, as the top timing.

Next, the swing analysis portion 211 sets an interval in which the combined value n(t) is equal to or smaller than a predetermined threshold value before and after the top time point $t_{top}$, as a top interval, and detects a last time point at which the combined value n(t) is equal to or smaller than the predetermined threshold value before a starting time point of the top interval, as a swing starting (backswing starting) time point $t_{start}$ (refer to FIG. 13). It is hardly considered that, in a typical golf swing, a swing action is started from a standing still state, and the swing action is stopped till the top. Therefore, the swing analysis portion 211 can capture the last timing at which the combined value of the angular velocities is equal to or smaller than the predetermined threshold value before the top interval as a timing of starting the swing action. The swing analysis portion 211 may detect a time point of the minimum point at which the combined value n(t) is close to 0 before the top time point $t_{top}$ as the swing starting time point $t_{start}$.

The swing analysis portion 211 may also detect each of a swing starting timing, a top timing, and an impact timing by using three-axis acceleration data in the same manner.

Calculation of Shaft Plane and Hogan Plane

The shaft plane is a first virtual plane specified by a target line (target hit ball direction) and the longitudinal direction of the shaft of the golf club 3 at address (standing still state)

of the user 2 before starting a swing. The Hogan plane is a second virtual plane specified by a virtual line connecting the vicinity of the shoulder (the shoulder or the base of the neck) of the user 2 to the head of the golf club (or the golf ball 4), and the target line (target hit ball direction), at address of the user 2.

Figure 15:
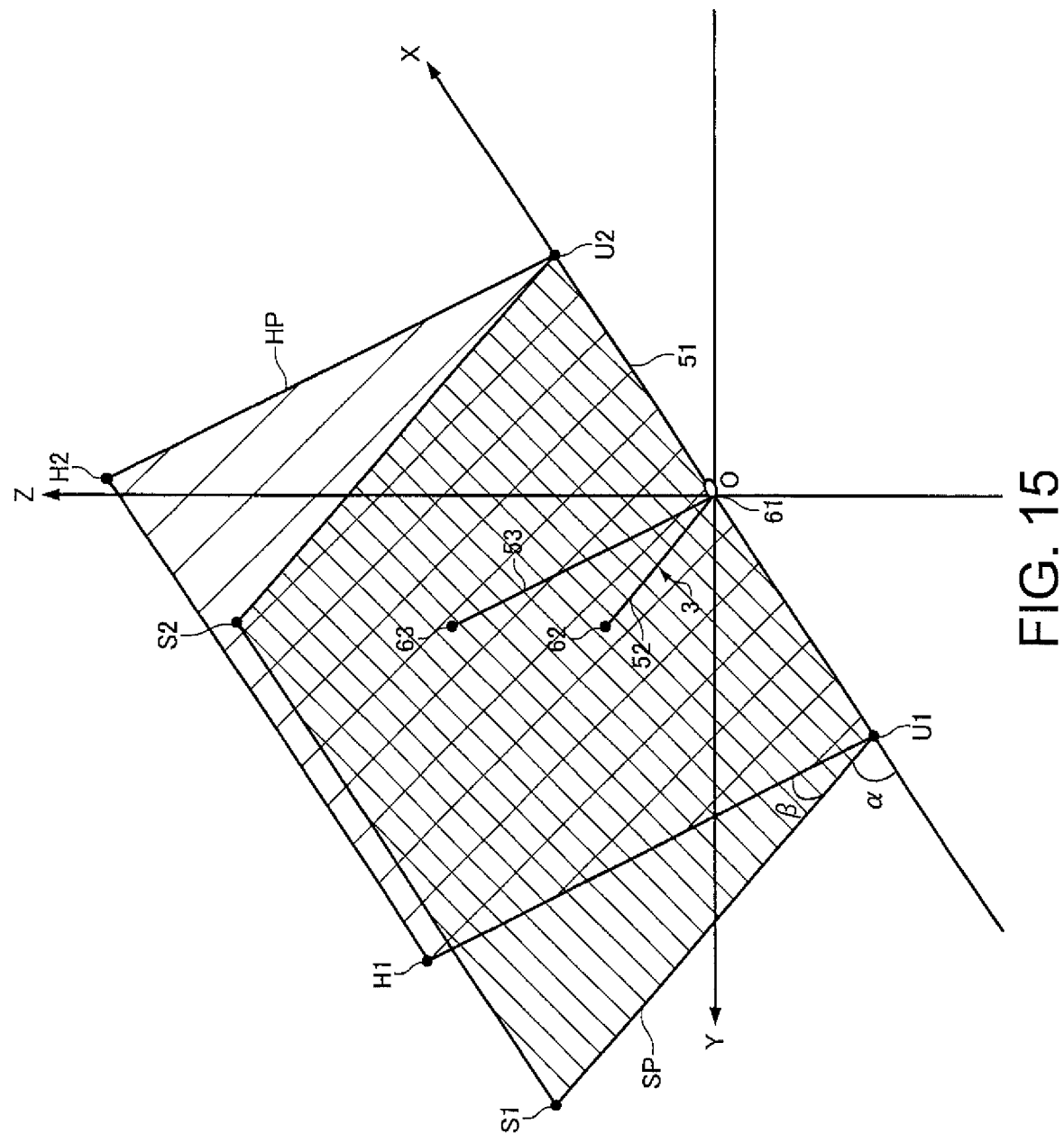
FIG. 15 is a diagram illustrating a shaft plane and a Hogan plane.

FIG. 15 is a diagram illustrating the shaft plane and the Hogan plane. FIG. 15 displays the X axis, the Y axis, and the Z axis of the XYZ coordinate system (global coordinate system).

As illustrated in FIG. 15, in the present embodiment, a virtual plane which includes a first line segment 51 as a first axis along a target hit ball direction and a second line segment 52 as a second axis along the longitudinal direction of the shaft of the golf club 3, and has four vertices such as U1, U2, S1, and S2, is used as the shaft plane SP (first virtual plane). In the present embodiment, the position 61 of the head of the golf club 3 at address is set as the origin O (0,0,0) of the XYZ coordinate system, and the second line segment 52 is a line segment connecting the position 61 (origin O) of the head of the golf club 3 to the position 62 of the grip end. The first line segment 51 is a line segment having a length UL in which U1 and U2 on the X axis are both ends, and the origin O is a midpoint. Since the user 2 performs the action in step S4 in FIG. 4 at address, and thus the shaft of the golf club 3 is perpendicular to the target line (X axis), the first line segment 51 is a line segment orthogonal to the longitudinal direction of the shaft of the golf club 3, that is, the second line segment 52. The swing analysis portion 211 calculates coordinates of the four vertices U1, U2, S1, and S2 of the shaft plane SP in the XYZ coordinate system.

Specifically, first, the swing analysis portion 211 computes coordinates $(0, G_Y, G_Z)$ of the position 62 of the grip end of the golf club 3 by using the inclined angle $\alpha$ and the length $L_1$ of the shaft included in the golf club information 242. As illustrated in FIG. 11, the swing analysis portion 211 may compute $G_Y$ and $G_Z$ by using the length $L_1$ of the shaft and the inclined angle $\alpha$ according to Equations (5) and (6).

$$G_Y = L_1 \cdot \cos \alpha \qquad (5)$$

$$G_Z = L_1 \cdot \sin \alpha \qquad (6)$$

Next, the swing analysis portion 211 multiplies the coordinates $(0, G_Y, G_Z)$ of the position 62 of the grip end of the golf club 3 by a scale factor S so as to compute coordinates $(0, S_Y, S_Z)$ of a midpoint S3 of the vertex S1 and the vertex S2 of the shaft plane SP. In other words, the swing analysis portion 211 computes $S_Y$ and $S_Z$ according to Equations (7) and (8), respectively.

$$S_Y = G_Y \cdot S \qquad (7)$$

$$S_Z = G_Z \cdot S \qquad (8)$$

Figure 16:
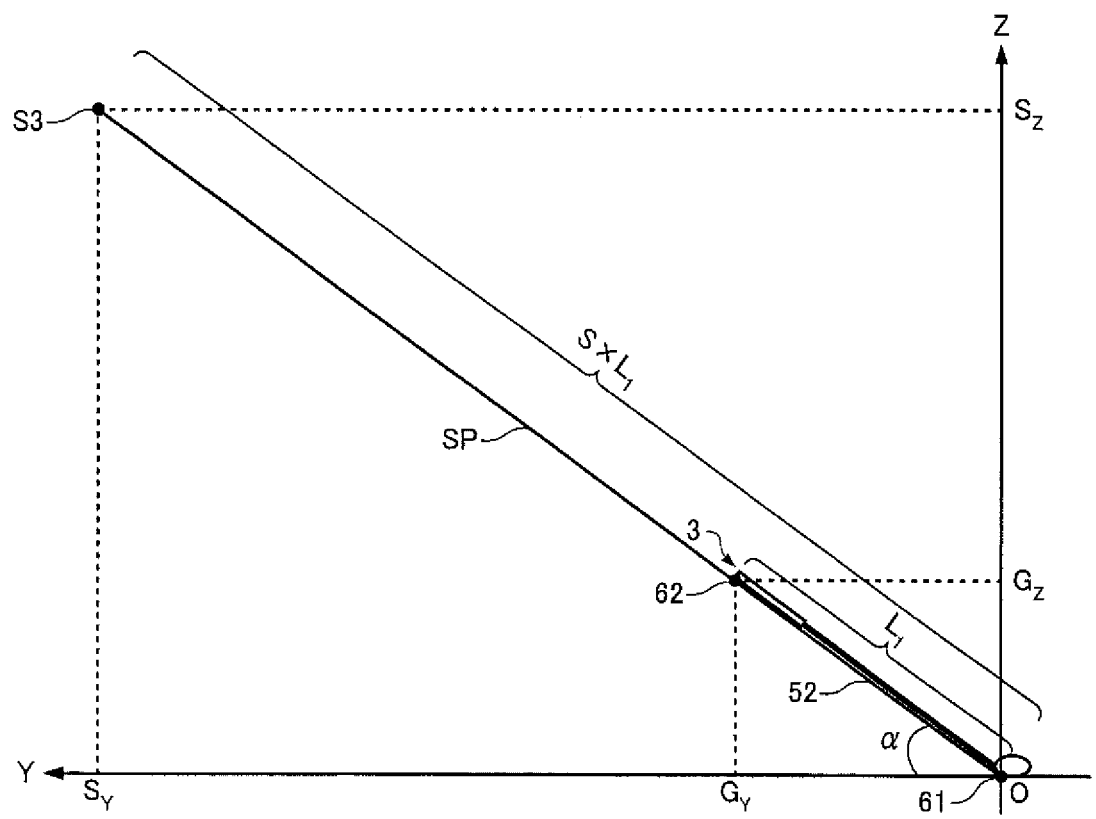
FIG. 16 is a view in which a sectional view of the shaft plane which is cut in a YZ plane is viewed from the negative side of the X axis.

FIG. 16 is a view in which a sectional view of the shaft plane SP in FIG. 15 which is cut in the YZ plane is viewed from the negative side of the X axis. As illustrated in FIG. 16, a length (a width of the shaft plane SP in a direction orthogonal to the X axis) of a line segment connecting the midpoint S3 of the vertex S1 and the vertex S2 to the origin O is S times the length $L_1$ of the second line segment 52. The scale factor S is set to a value at which a trajectory of the golf club 3 during a swing action of the user 2 enters the shaft plane SP. For example, if a length of the arms of the user 2 is indicated by $L_2$, the scale factor S may be set as in Equation (9) so that the width $S \times L_1$ of the shaft plane SP in the direction orthogonal to the X axis is twice the sum of the length $L_1$ of the shaft and the length $L_2$ of the arms.

$$S = \frac{2 \cdot (L_1 + L_2)}{L_1} \qquad (9)$$

The length $L_2$ of the arms of the user 2 is associated with a height $L_0$ of the user 2. The length $L_2$ of the arms is expressed by a correlation expression such as Equation (10) in a case where the user 2 is a male, and is expressed by a correlation expression such as Equation (11) in a case where the user 2 is a female, on the basis of statistical information.

$$L_2 = 0.41 \times L_0 - 45.5 \text{[mm]} \qquad (10)$$

$$L_2 = 0.46 \times L_0 - 126.9 \text{[mm]} \qquad (11)$$

Therefore, the swing analysis portion 211 may calculate the length $L_2$ of the arms of the user according to Equation (10) or Equation (11) by using the height $L_0$ and the sex of the user 2 included in the physical information 244.

Next, the swing analysis portion 211 computes coordinates (−UL/2,0,0) of the vertex U1 of the shaft plane SP, coordinates (UL/2,0,0) of a vertex U2, coordinates (−UL/2, $S_Y, S_Z$) of the vertex S1, and coordinates (UL/2, $S_Y, S_Z$) of the vertex S2 by using the coordinates $(0, S_Y, S_Z)$ of the midpoint S3 and a width (the length of the first line segment 51) UL of the shaft plane SP in the X axis direction. The width UL in the X axis direction is set to a value at which a trajectory of the golf club 3 during a swing action of the user 2 enters the shaft plane SP. For example, the width UL in the X axis direction may be set to be the same as the width $S \times L_1$ in the direction orthogonal to the X axis, that is, twice the sum of the length $L_1$ of the shaft and the length $L_2$ of the arms.

In the above-described manner, the swing analysis portion 211 can calculate the coordinates of the four vertices U1, U2, S1, and S2 of the shaft plane SP.

As illustrated in FIG. 15, in the present embodiment, a virtual plane which includes a first line segment 51 as a first axis and a third line segment 53 as a third axis, and has four vertices such as U1, U2, H1, and H2, is used as the Hogan plane HP (second virtual plane). The third line segment 53 is a line segment connecting a predetermined position 63 in the vicinity of a line segment connecting both of the shoulders of the user 2, to the position 61 of the head of the golf club 3. However, the third line segment 53 may be a line segment connecting the predetermined position 63 to a position of the golf ball 4. The swing analysis portion 211 calculates respective coordinates of the four vertices U1, U2, H1, and H2 of the Hogan plane HP in the XYZ coordinate system.

Specifically, first, the swing analysis portion 211 estimates the predetermined position 63 by using the coordinates $(0, G_Y, G_Z)$ of the position 62 of the grip end of the golf club 3 at address (during standing still), and the length $L_2$ of the arms of the user 2 based on the physical information 244, and computes coordinates $(A_X, A_Y, A_Z)$ thereof.

Figure 17:
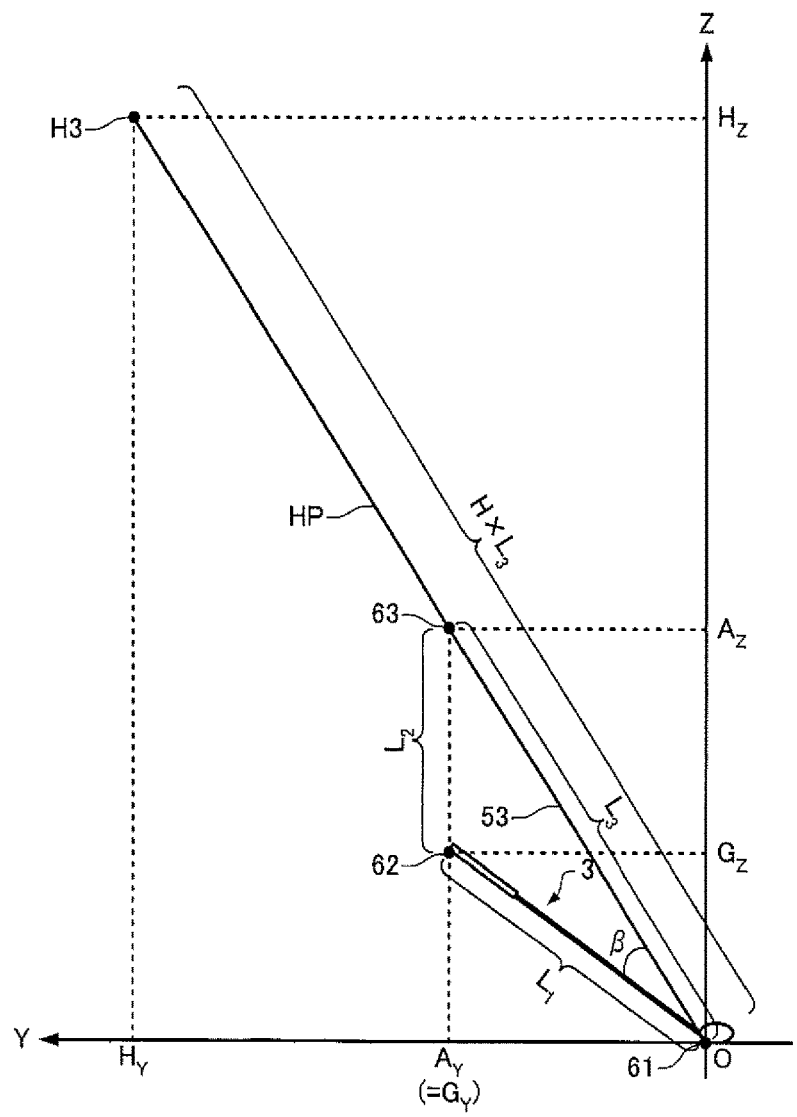
FIG. 17 is a view in which a sectional view of the Hogan plane which is cut in the YZ plane is viewed from the negative side of the X axis.

FIG. 17 is a view in which a sectional view of the Hogan plane HP illustrated in FIG. 15 which is cut in the YZ plane is viewed from the negative side of the X axis. In FIG. 17, a midpoint of the line segment connecting both of the shoulders of the user 2 is the predetermined position 63, and the predetermined position 63 is present on the YZ plane. Therefore, an X coordinate $A_X$ of the predetermined position 63 is 0. As illustrated in FIG. 17, the swing analysis portion 211 estimates, as the predetermined position 63, a position obtained by moving the position 62 of the grip end of the golf club 3 by the length $L_2$ of the arms of the user 2 in a positive direction along the Z axis. Therefore, the swing analysis portion 211 sets a Y coordinate $A_Y$ of the predetermined position 63 to be the same as the Y coordinate $G_Y$ of the position 62 of the grip end. The swing analysis portion 211 computes a Z coordinate $A_Z$ of the predetermined position 63 as a sum of the Z coordinate $G_Z$ of the position 62 of the grip end and the length $L_2$ of the arms of the user 2 as in Equation (12).

$$A_Z = G_Z + L_2 \quad (12)$$

Next, the swing analysis portion 211 multiplies the Y coordinate $A_Y$ and the Z coordinate $A_Z$ of the predetermined position 63 by a scale factor H, so as to compute coordinates $(0, H_Y, H_Z)$ of a midpoint H3 of the vertex H1 and the vertex H2 of the Hogan plane HP. In other words, the swing analysis portion 211 computes $H_Y$ and $H_Z$ according to Equation (13) and Equation (14), respectively.

$$H_Y = A_Y \cdot H \quad (13)$$

$$H_Z = A_Z \cdot H \quad (14)$$

As illustrated in FIG. 17, a length (a width of the Hogan plane HP in a direction orthogonal to the X axis) of a line segment connecting the midpoint H3 of the vertex H1 and the vertex H2 to the origin O is H times the length $L_3$ of the third line segment 53. The scale factor H is set to a value at which a trajectory of the golf club 3 during a swing action of the user 2 enters the Hogan plane HP. For example, the Hogan plane HP may have the same shape and size as the shape and the size of the shaft plane SP. In this case, the width $H \times L_3$ of the Hogan plane HP in the direction orthogonal to the X axis matches the width $S \times L_1$ of the shaft plane SP in the direction orthogonal to the X axis, and is twice the sum of the length $L_1$ of the shaft of the golf club 3 and the length $L_2$ of the arms of the user 2. Therefore, the swing analysis portion 211 may compute the scale factor H according to Equation (15).

$$H = \frac{2 \cdot (L_1 + L_2)}{L_3} \quad (15)$$

The swing analysis portion 211 may compute the length $L_3$ of the third line segment 53 according to Equation (13) by using the Y coordinate $A_Y$ and the Z coordinate $A_Z$ of the predetermined position 63.

Next, the swing analysis portion 211 computes coordinates $(-UL/2, H_Y, H_Z)$ of the vertex H1 of the Hogan plane HP, and coordinates $(UL/2, H_Y, H_Z)$ of the vertex H2 by using the coordinates $(0, H_Y, H_Z)$ of the midpoint H3 and a width (the length of the first line segment 51) UL of the Hogan plane HP in the X axis direction. The two vertices U1 and U2 of the Hogan plane HP are the same as those of the shaft plane SP, and thus the swing analysis portion 211 does not need to compute coordinates of the vertices U1 and U2 of the Hogan plane HP again.

In the above-described manner, the swing analysis portion 211 can calculate the coordinates of the four vertices U1, U2, H1, and H2 of the Hogan plane HP.

A region interposed between the shaft plane SP (first virtual plane) and the Hogan plane HP (second virtual plane) is referred to as a "V zone", and a trajectory of a hit ball (a ball line) may be estimated to some extent on the basis of a relationship between a position of the head of the golf club 3 and the V zone during backswing or downswing. For example, in a case where the head of the golf club 3 is present in a space lower than the V zone at a predetermined timing during a backswing or downswing, a hit ball is likely to fly in a hook direction. In a case where the head of the golf club 3 is present in a space higher than the V zone at a predetermined timing during a backswing or downswing, a hit ball is likely to fly in a slice direction. In the present embodiment, as is clear from FIG. 17, a first angle $\beta$ formed between the shaft plane SP and the Hogan plane HP is determined depending on the length $L_1$ of the shaft of the golf club 3 and the length $L_2$ of the arms of the user 2. In other words, since the first angle $\beta$ is not a fixed value, and is determined depending on the type of golf club 3 or physical features of the user 2, the more appropriate shaft plane SP and Hogan plane HP (V zone) are calculated as an index for diagnosing a swing of the user 2.

Calculation of Head Positions at Halfway Back and Halfway Down

A head position at halfway back is a position of the head at the moment of the halfway back, right before the halfway back, or right after the halfway back, and a head position at halfway down is a position of the head at the moment of the halfway down, right before the halfway down, or right after the halfway down.

First, the swing analysis portion 211 computes a position of the head and a position of the grip end at each time point t by using the position and the attitude of the sensor unit 10 at each time point t from the swing start time point $t_{start}$ to the impact time point $t_{impact}$.

Specifically, the swing analysis portion 211 uses a position separated by the distance Ls in the positive direction of the y axis specified by the attitude of the sensor unit 10, from the position of the sensor unit 10 at each time point t as a position of the head, and computes coordinates of the position of the head. As described above, the distance $L_{SH}$ is a distance between the sensor unit 10 and the head. The swing analysis portion 211 uses a position separated by the distance $L_{SG}$ in the negative direction of the y axis specified by the attitude of the sensor unit 10, from the position of the sensor unit 10 at each time point t as a position of the grip end, and computes coordinates of the position of the grip end. As described above, the distance $L_{SG}$ is a distance between the sensor unit 10 and the grip end.

Next, the swing analysis portion 211 detects a halfway back timing and a halfway down timing by using the coordinates of the position of the head and the coordinates of the position of the grip end.

Specifically, the swing analysis portion 211 computes a difference $\Delta Z$ between a Z coordinate of the position of the head and a Z coordinate of the position of the grip end at each time point t from the swing start time point $t_{start}$ to the impact time point $t_{impact}$. The swing analysis portion 211 detects a time point $t_{HWB}$ at which a sign of $\Delta Z$ is inversed between the swing start time point $t_{start}$ and the top time point $t_{top}$, as the halfway back timing. The swing analysis portion 211 detects a time point $t_{HWD}$ at which a sign of $\Delta Z$ is inversed between the top time point $t_{top}$ and the impact time point $t_{impact}$, as the halfway down timing.

The swing analysis portion 211 uses the position of the head at the time point $t_{HWB}$ as a position of the head at halfway back, and uses the position of the head at the time point $t_{HWD}$ as a position of the head at halfway down.

Calculation of Head Speed

A head speed is the magnitude of a speed of the head at impact (the moment of the impact, right before the impact, or right after the impact). For example, the swing analysis portion 211 computes a speed of the head at the impact time point $t_{impact}$ on the basis of differences between the coordinates of the position of the head at the impact time point $t_{impact}$ and coordinates of a position of the head at the previous time point. The swing analysis portion 211 computes the magnitude of the speed of the head as the head speed.

Calculation of Face Angle and Club Path (Incidence Angle)

The face angle is an index based on an inclination of the head of the golf club 3 at impact, and the club path (incidence angle) is an index based on a trajectory of the head of the golf club 3 at impact.

Figure 18:
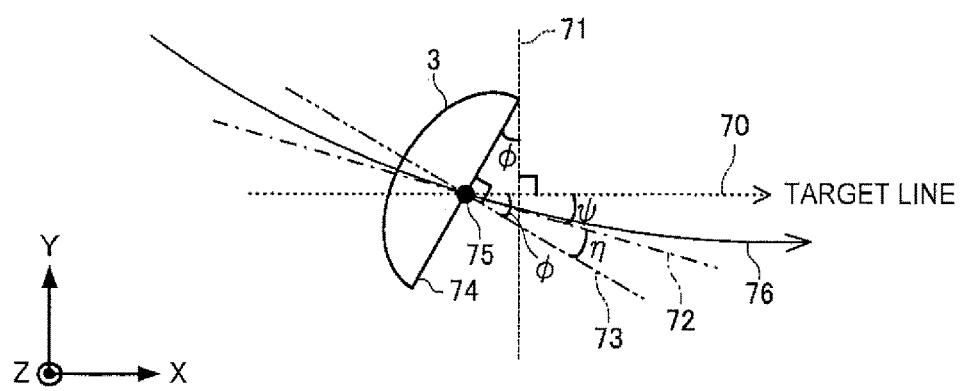
FIG. 18 is a diagram for explaining a face angle and a club path (incidence angle).

FIG. 18 is a diagram for explaining the face angle and the club path (incidence angle). FIG. 18 illustrates the golf club 3 (only the head is illustrated) on the XY plane viewed from a positive side of the Z axis in the XYZ coordinate system. In FIG. 18, the reference numeral 74 indicates a face surface (hitting surface) of the golf club 3, and the reference numeral 75 indicates a ball hitting point. The reference numeral 70 indicates a target line indicating a target hit ball direction, and the reference numeral 71 indicates a plane orthogonal to the target line 70. The reference numeral 76 indicates a curve indicating a trajectory of the head of the golf club 3, and the reference numeral 72 is a tangential line at the ball hitting point 75 for the curve 76. In this case, the face angle ϕ is an angle formed between the plane 71 and the face surface 74, that is, an angle formed between a straight line 73 orthogonal to the face surface 74, and the target line 70. The club path (incidence angle) ψ is an angle formed between the tangential line 72 (a direction in which the head in the XY plane passes through the ball hitting point 75) and the target line 70.

For example, assuming that an angle formed between the face surface of the head and the x axis direction is normally constant (for example, orthogonal), the swing analysis portion 211 computes a direction of a straight line orthogonal to the face surface on the basis of the attitude of the sensor unit 10 at the impact time point $t_{impact}$. The swing analysis portion 211 uses, a straight line obtained by setting a Z axis component of the direction of the straight line to 0, as a direction of the straight line 73, and computes an angle (face angle) ϕ formed between the straight line 73 and the target line 70.

For example, the swing analysis portion 211 uses a direction of a speed (that is, a speed of the head in the XY plane) obtained by setting a Z axis component of a speed of the head at the impact time point $t_{impact}$ to 0, as a direction of the tangential line 72, and computes an angle (club path (incidence angle)) ψ formed between the tangential line 72 and the target line 70.

The face angle ϕ indicates an inclination of the face surface 74 with the target line 70 whose direction is fixed regardless of an incidence direction of the head to the ball hitting point 75 as a reference, and is thus also referred to as an absolute face angle. In contrast, an angle η formed between the straight line 73 and the tangential line 72 indicates an inclination of the face surface 74 with an incidence direction of the head to the ball hitting point 75 as a reference, and is thus referred to as a relative face angle. The relative face angle η is an angle obtained by subtracting the club path (incidence angle) ψ from the (absolute) face angle ϕ.

Calculation of Shaft Axis Rotation Angle at Top

The shaft axis rotation angle $\theta_{top}$ at top is an angle (relative rotation angle) by which the golf club 3 is rotated about a shaft axis from a reference timing to a top timing. The reference timing is, for example, the time of starting a backswing, or the time of address. In the present embodiment, in a case where the user 2 is a right-handed golfer, a right-handed screw tightening direction toward the tip end on the head side of the golf club 3 (a clockwise direction when the head is viewed from the grip end side) is a positive direction of the shaft axis rotation angle $\theta_{top}$. Conversely, in a case where the user 2 is a left-handed golfer, a left-handed screw tightening direction toward the tip end on the head side of the golf club 3 (a counterclockwise direction when the head is viewed from the grip end side) is a positive direction of the shaft axis rotation angle $\theta_{top}$.

Figure 19:
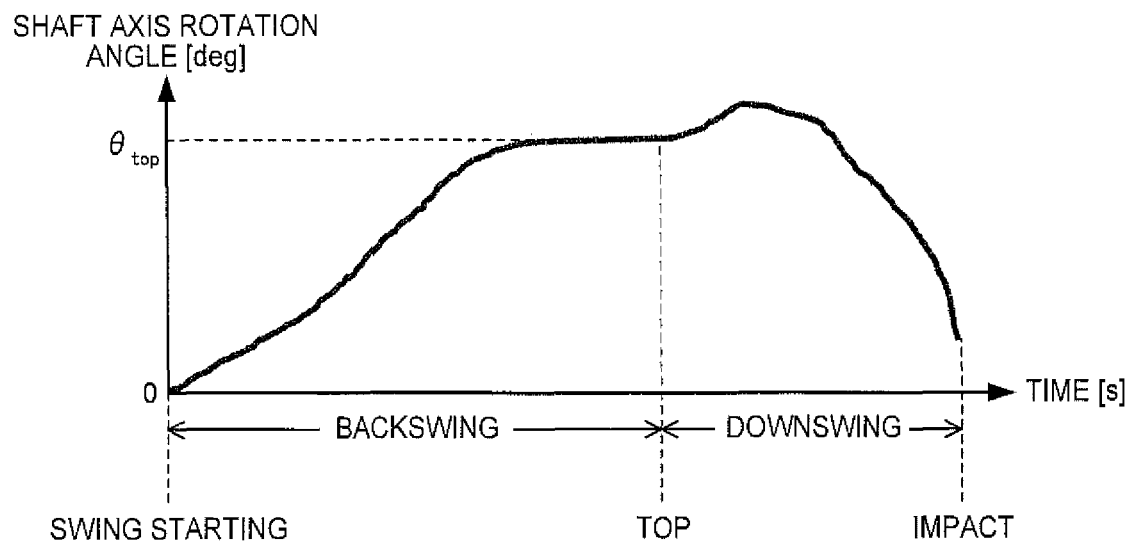
FIG. 19 is a diagram illustrating an example of a temporal change of a shaft axis rotation angle from swing starting (backswing starting) to impact.

FIG. 19 is a diagram illustrating an example of a temporal change of the shaft axis rotation angle from starting of a swing (starting of a backswing) to impact. In FIG. 19, a transverse axis expresses time (s), and a longitudinal axis expresses a shaft axis rotation angle (deg). FIG. 19 illustrates the shaft axis rotation angle $\theta_{top}$ at top with the time of starting a swing (the time of starting a backswing) as a reference timing (at which the shaft axis rotation angle is 0°).

In the present embodiment, as illustrated in FIG. 3, the y axis of the sensor unit 10 substantially matches the long axis direction of the shaft of the golf club 3 (the long axis direction of the golf club 3). Therefore, for example, the swing analysis portion 211 time-integrates a y axis angular velocity included in angular velocity data from the swing starting (backswing starting) time point $t_{start}$ or the time of address to the top time point $t_{top}$ (at top), so as to compute the shaft axis rotation angle $\theta_{top}$.

Calculation of Grip Deceleration Ratio and Grip Deceleration Time Ratio

The grip deceleration ratio is an index based on a grip deceleration amount, and is a ratio between a speed of the grip when the grip starts to be decelerated during the downswing, and a speed of the grip at impact. The grip deceleration time ratio is an index based on a grip deceleration period, and is a ratio between a period of time from the time at which the grip starts to be decelerated during the downswing to the time of impact, and a period of time of the downswing. A speed of the grip is preferably a speed of a portion held by the user 2, but may be a speed of any portion of the grip (for example, the grip end), and may be a speed of a peripheral portion of the grip.

Figure 20:
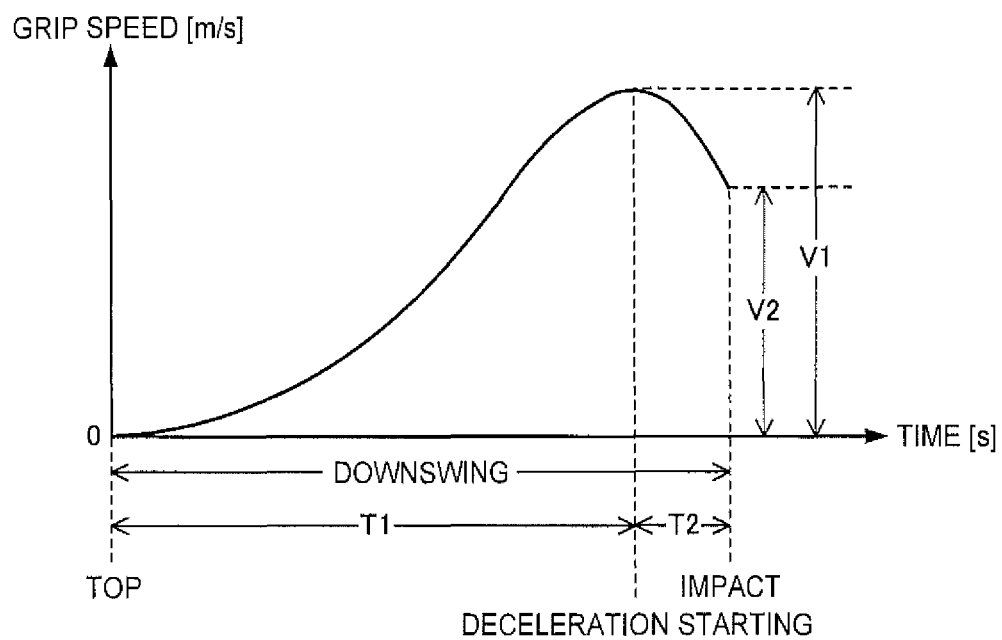
FIG. 20 is a diagram illustrating an example of a temporal change of a speed of a grip in a downswing.

FIG. 20 is a diagram illustrating an example of a temporal change of a speed of the grip during the downswing. In FIG. 20, a transverse axis expresses time (s), and a longitudinal axis expresses a speed (m/s) of the grip. In FIG. 20, if a speed (the maximum speed of the grip) when the grip starts to be decelerated is indicated by V1, and a speed of the grip at impact is indicated by V2, a grip deceleration ratio $R_V$ (unit: %) is expressed by the following Equation (16).

$$R_V = \frac{V1 - V2}{V1} \times 100(\%) \qquad (16)$$

In FIG. 20, if a period of time from the time of top to the time at which the grip starts to be decelerated is indicated by T1, and a period of time from the time at which the grip starts to be decelerated during the downswing to the time of impact is indicated by T2, a grip deceleration time ratio $R_T$ (unit: %) is expressed by the following Equation (17).

$$R_T = \frac{T2}{T1 + T2} \times 100(\%) \qquad (17)$$

For example, the sensor unit 10 may be attached to the vicinity of a portion of the golf club 3 held by the user 2, and a speed of the sensor unit 10 may be regarded as a speed of the grip. Therefore, first, the swing analysis portion 211 computes a speed of the sensor unit 10 at the time point t on the basis of differences between coordinates of a position of the sensor unit 10 at each time point t from the top time point $t_{top}$ to the impact time point $t_{impact}$ (during the downswing), and coordinates of a position of the sensor unit 10 at the previous time point.

Next, the swing analysis portion 211 computes the magnitude of the speed of the sensor unit 10 at each time point t, sets the maximum value thereof as V1, and sets the magnitude of the speed at the impact time point $t_{impact}$ as V2. The swing analysis portion 211 specifies a time point $t_{vmax}$ at which the magnitude of the speed of the sensor unit 10 becomes the maximum value V1. The swing analysis portion 211 computes $T1=t_{vmax}-t_{top}$, and $T2=t_{impact}-t_{vmax}$. The swing analysis portion 211 computes the grip deceleration ratio $R_V$ and the grip deceleration time ratio $R_T$ according to Equations (16) and (17), respectively.

The swing analysis portion 211 may regard a speed of the grip end as a speed of the grip, and may compute the speed of the grip end on the basis of coordinates of a position of the grip end at each time point t during the downswing, so as to obtain the grip deceleration ratio $R_V$ and the grip deceleration time ratio $R_T$ through the above-described computation.

Procedures of Swing Analysis Process (Swing Analysis Method)

Figure 21:
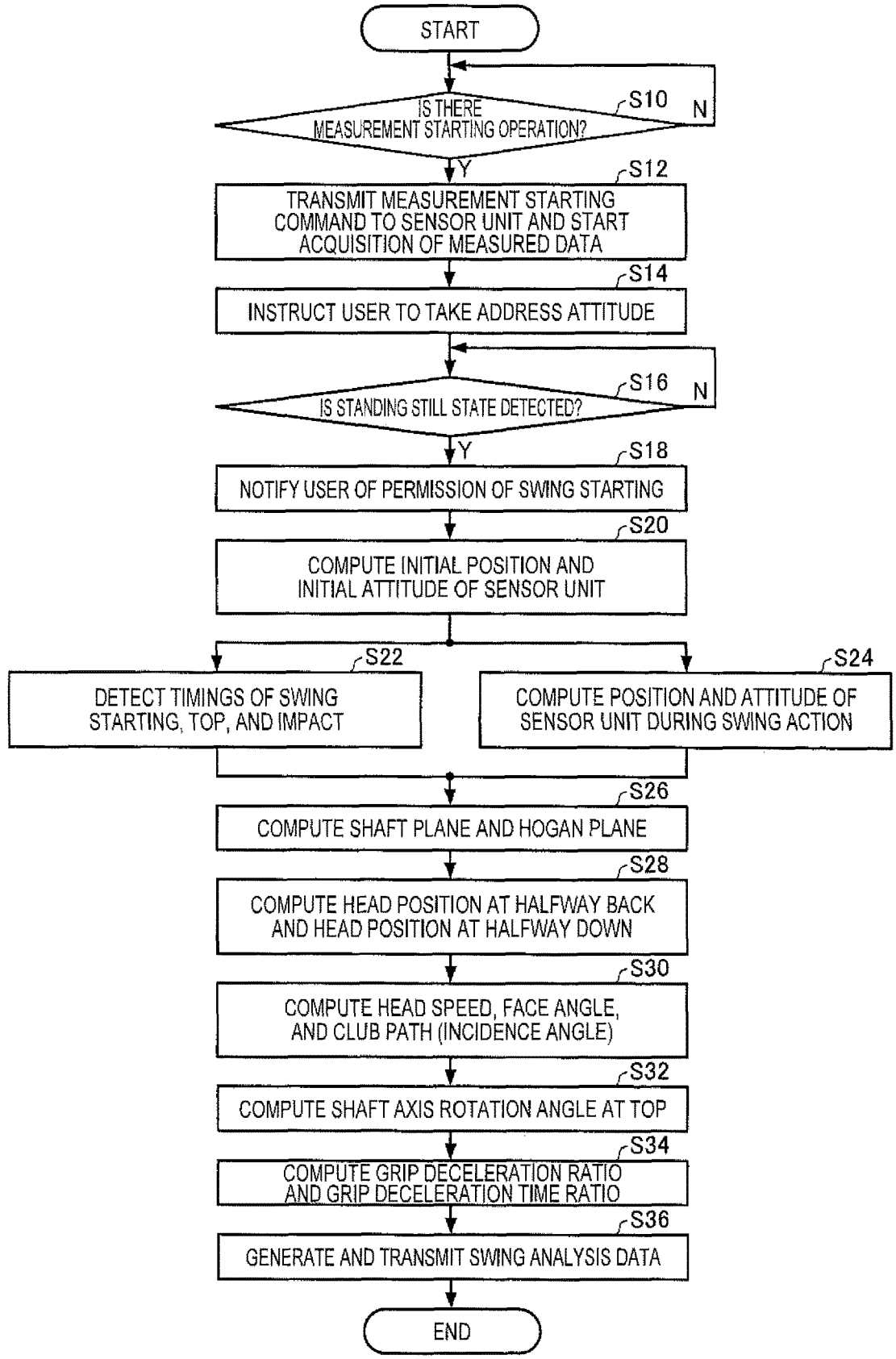
FIG. 21 is a flowchart illustrating examples of procedures of a swing analysis process (swing analysis method).

FIG. 21 is a flowchart illustrating examples of procedures of a swing analysis process (swing analysis method) performed by the processing section 21. The processing section 21 performs the swing analysis process, for example, according to the procedures shown in the flowchart of FIG. 21 by executing the swing analysis program 240 stored in the storage section 24. Hereinafter, the flowchart of FIG. 21 will be described.

First, the processing section 21 waits for the user 2 to perform a measurement starting operation (the operation in step S2 in FIG. 4) (N in step S10), transmits a measurement starting command to the sensor unit 10 if the measurement starting operation is performed (Y in step S10), and starts to acquire measured data from the sensor unit 10 (step S12).

Next, the processing section 21 instructs the user 2 to take an address attitude (step S14). The user 2 takes the address attitude in response to the instruction, and stands still (step S4 in FIG. 4).

Next, if a standing still state of the user 2 is detected by using the measured data acquired from the sensor unit 10 (Y in step S16), the processing section 21 notifies the user 2 of permission of swing starting (step S18). The processing section 21 outputs, for example, a predetermined sound, or an LED is provided in the sensor unit 10, and the LED is lighted, so that the user 2 is notified of permission of swing starting. The user 2 confirms the notification and then starts a swing action (the action in step S6 in FIG. 4).

Next, the processing section 21 performs processes in step S20 and subsequent steps after completion of the swing action of the user 2, or from before completion of the swing action.

First, the processing section 21 computes an initial position and an initial attitude of the sensor unit 10 by using the measured data (measured data during standing still (at address) of the user 2) acquired from the sensor unit 10 (step S20).

Next, the processing section 21 detects a swing starting timing, a top timing, and an impact timing by using the measured data acquired from the sensor unit 10 (step S22).

The processing section 21 computes a position and an attitude of the sensor unit 10 during the swing action of the user 2 in parallel to the process in step S22, or before and after the process in step S22 (step S24).

Next, in steps S26 to S34, the processing section 21 computes values of various indexes regarding the swing by using at least some of the measured data acquired from the sensor unit 10, the swing starting, top and impact timings detected in step S22, and the position and the attitude of the sensor unit 10 computed in step S24.

The processing section 21 computes the shaft plane SP and the Hogan plane HP in step S26.

The processing section 21 computes a head position at halfway back and a head position at halfway down in step S28.

The processing section 21 computes a head speed, the face angle φ, and the club path (incidence angle) ψ in step S30.

The processing section 21 computes the shaft axis rotation angle $θ_{top}$ at top in step S32.

The processing section 21 computes the grip deceleration ratio $R_V$ and the grip deceleration time ratio $R_T$ in step S34.

The processing section 21 generates the swing analysis data 248 by using the various indexes calculated in steps S26 to S34, transmits the swing analysis data to the swing diagnosis apparatus 30 (step S36), and finishes the swing analysis process.

In the flowchart of FIG. 21, order of the respective steps may be changed as appropriate within an allowable range, some of the steps may be omitted or changed, and other steps may be added thereto.

1-4. Configuration of Swing Diagnosis Apparatus

Figure 22:
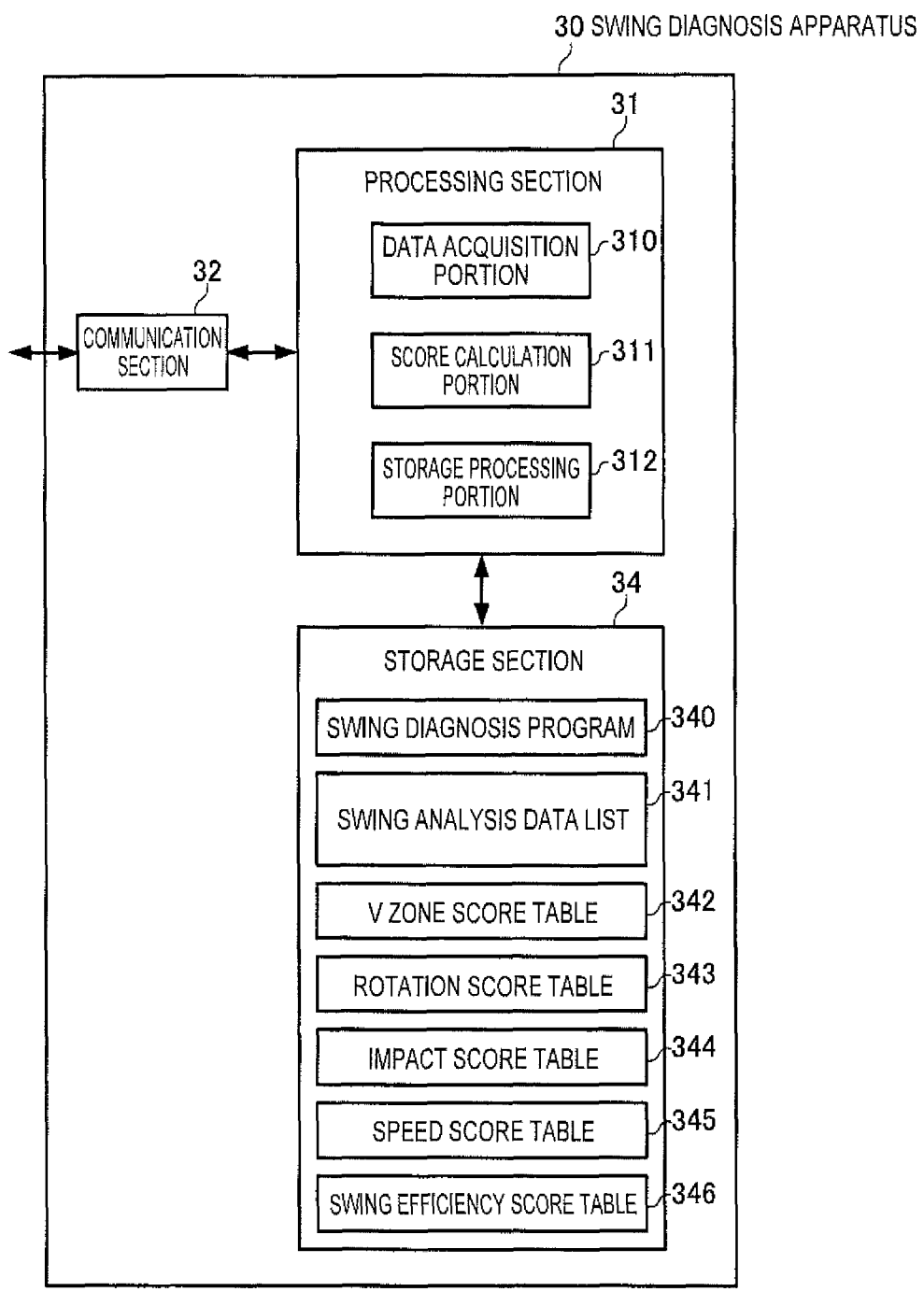
FIG. 22 is a diagram illustrating a configuration example of a swing diagnosis apparatus.

FIG. 22 is a diagram illustrating a configuration example of the swing diagnosis apparatus 30. As illustrated in FIG. 22, in the present embodiment, the swing diagnosis apparatus 30 is configured to include a processing section 31, a communication section 32, and a storage section 34. However, the swing diagnosis apparatus 30 may have a configuration in which some of the constituent elements are deleted or changed as appropriate, or may have a configuration in which other constituent elements are added thereto.

The storage section 34 is constituted of, for example, various IC memories such as a ROM, a flash ROM, and a RAM, or a recording medium such as a hard disk or a memory card. The storage section 34 stores a program for the processing section 31 performing various calculation processes or a control process, or various programs or data for realizing application functions.

In the present embodiment, the storage section 34 stores a swing diagnosis program 340 which is read by the processing section 31 and executes a swing diagnosis process. The swing diagnosis program 340 may be stored in a nonvolatile recording medium (computer readable recording medium) in advance, or the swing diagnosis program 340 may be received from a server (not illustrated) by the processing section 31 via a network, and may be stored in the storage section 34.

In the present embodiment, the storage section 34 stores (preserves) a swing analysis data list 341 including a plurality of items of swing analysis data 248 generated by the swing analysis apparatus 20. In other words, the swing analysis data 248 generated whenever the processing section 21 of the swing analysis apparatus 20 analyzes a swing action of the user 2 is sequentially added to the swing analysis data list 341.

In the present embodiment, the storage section 34 stores a V zone score table 342, a rotation score table 343, an impact score table 344, a speed score table 345, and a swing efficiency score table 346. The score tables will be described later in detail.

The storage section 34 is used as a work area of the processing section 31, and temporarily stores results of calculation executed by the processing section 31 according to various programs, and the like. The storage section 34 may store data which is required to be preserved for a long period of time among data items generated through processing of the processing section 31.

The communication section 32 performs data communication with the communication section 27 (refer to FIG. 10) of the swing analysis apparatus 20 via the network 40. For example, the communication section 32 performs a process of receiving the swing analysis data 248 from the communication section 27 of the swing analysis apparatus 20, and transmitting the swing analysis data 248 to the processing section 31. For example, the communication section 32 performs a process of transmitting information required to display the selection screen illustrated in FIG. 7 to the communication section 27 of the swing analysis apparatus 20, or a process of receiving selected information on the selection screen illustrated in FIG. 7 from the communication section 27 of the swing analysis apparatus 20 and transmitting the selected information to the processing section 31. For example, the communication section 32 performs a process of receiving information required to display the input data editing screen illustrated in FIG. 8 from the processing section 31, and transmitting the information to the communication section 27 of the swing analysis apparatus 20. For example, the communication section 32 performs a process of receiving input data at the time of the diagnosis starting button on the input data editing screen illustrated in FIG. 8 being pressed from the communication section 27 of the swing analysis apparatus 20, transmitting the input data to the processing section 31, receiving diagnosis result information (scores or a total score of a plurality of items indicating features of a swing of the user 2) based on the input data from the processing section 31, and transmitting the diagnosis result information to the communication section 27 of the swing analysis apparatus 20. For example, the communication section 32 performs a process of receiving information required to display the swing diagnosis screen illustrated in FIG. 9 from the processing section 31, and transmitting the information to the communication section 27 of the swing analysis apparatus 20.

The processing section 31 performs a process of receiving the swing analysis data 248 from the swing analysis apparatus 20 via the communication section 32 and storing the swing analysis data 248 in the storage section 34 (adding the swing analysis data to the swing analysis data list 341), according to various programs. The processing section 31 performs a process of receiving various pieces of information from the swing analysis apparatus 20 via the communication section 32, and transmitting information required to display various screens (the respective screens illustrated in FIGS. 7, 8 and 9) to the swing analysis apparatus 20, according to various programs. The processing section 31 performs other various control processes.

Particularly, in the present embodiment, the processing section 31 functions as a data acquisition portion 310, a score calculation portion 311, and a storage processing portion 312 by executing the swing diagnosis program 340, and performs a diagnosis process (swing diagnosis process) on the swing analysis data 248 selected from the swing analysis data list 341.

The data acquisition portion 310 performs a process of receiving the swing analysis data 248 received from the swing analysis apparatus 20 by the communication section 32 and transmitting the swing analysis data 248 to the storage processing portion 312. The data acquisition portion 310 performs a process of receiving various pieces of information received from the swing analysis apparatus 20 by the communication section 32 and transmitting the information to the score calculation portion 311.

The storage processing portion 312 performs read/write processes of various programs or various data for the storage section 34. The storage processing portion 312 performs a process of receiving the swing analysis data 248 from the data acquisition portion 310 and storing the swing analysis data 248 in the storage section 34 (adding the swing analysis data to the swing analysis data list 341), a process of reading the swing analysis data 248 from the swing analysis data list 341 stored in the storage section 34, or the like. For example, the storage processing portion 312 performs a process of reading the V zone score table 342, the rotation score table 343, the impact score table 344, the speed score table 345, and the swing efficiency score table 346 stored in the storage section 34.

The score calculation portion 311 (level calculation section) performs a process of calculating scores (levels) of a plurality of items on the basis of data regarding a swing. In the present embodiment, the data regarding a swing may be input data at the time of the diagnosis starting button on the input data editing screen illustrated in FIG. 8 being pressed, may be the swing analysis data 248 selected on the selection screen illustrated in FIG. 7, and may include both of the data.

For example, in a case where the sex, the type of golf club, and each index of a swing are not edited in a state of being initial values, and the diagnosis starting button is pressed on the input data editing screen illustrated in FIG. 8, the score calculation portion 311 performs a process of calculating scores on the basis of the swing analysis data 248 selected from the swing analysis data list 341. On the other hand, in a case where at least one of the sex, the type of golf club, and each index of a swing is edited, and then the diagnosis starting button is pressed on the input data editing screen illustrated in FIG. 8, the score calculation portion 311 performs a process of calculating scores on the basis of data (pseudo-data) in which at least a part of the selected swing analysis data 248 is edited.

A plurality of items which are score calculation targets include a first item regarding at least one of a backswing and a downswing. The first item may include an item indicating a relationship among at least one virtual plane, a position of the head (an example of a ball hitting portion) of the golf club 3 (an example of an exercise appliance) at a first timing during the backswing, and a position of the head at a second timing during the downswing. For example, the first timing may be the time at which the long axis direction of the golf club 3 becomes a direction along the horizontal direction during the backswing. For example, the second timing may be the time at which the long axis direction of the golf club 3 becomes a direction along the horizontal direction during the downswing.

At least one virtual plane may include the shaft plane SP which is a first virtual plane specified on the basis of the first line segment 51 which is a first axis along a target hit ball direction (target line) in the XY plane as a reference plane, and the second line segment 52 which is a second axis along the long axis direction of the golf club 3 before starting a backswing. The time before starting a backswing may be the time of address (when the user 2 takes an address attitude and stands still).

At least one virtual plane may include the Hogan plane HP which is a second virtual plane (that is, the second virtual plane forms a first angle β with the first virtual plane) specified on the basis of the first line segment 51 which is a first axis along a target hit ball direction (target line) in the XY plane as a reference plane, and the third line segment 53 which is a third axis forming the first angle β with the long axis direction of the golf club 3 before starting a backswing.

At least one virtual plane may include only one of the shaft plane SP and the Hogan plane HP. At least one virtual plane may include other virtual planes (for example, a plane interposed between the shaft plane SP and the Hogan plane HP, a plane outside the shaft plane SP and the Hogan plane HP, and a plane intersecting at least one of the shaft plane SP and the Hogan plane HP) instead of the shaft plane SP or the Hogan plane HP.

Hereinafter, the first item is assumed to include an item (hereinafter, this item will be referred to as a "V zone" item) indicating a relationship among four indexes of a swing, that is, the "shaft plane SP", the "Hogan plane HP", a "position of the head at halfway back", and a "position of the head at halfway down".

The first item may include an item regarding swing efficiency. The item regarding swing efficiency may be an item indicating a relationship between a deceleration amount and a deceleration period of the grip (an example of a holding portion) of the golf club 3 in a downswing. Hereinafter, the first item is assumed to include an item (hereinafter, this item will be referred to as a "swing efficiency" item) indicating a relationship between a "grip deceleration ratio" which is an index based on the deceleration amount of the grip and a "grip deceleration time ratio" which is an index based on the deceleration period of the grip, as the item regarding swing efficiency.

The plurality of items which are score calculation targets also include a second item regarding impact (at ball hitting). The second item may include an item indicating a relationship between an incidence angle of the head of the golf club 3 and an inclination of the head at impact (at ball hitting). Hereinafter, the second item is assumed to include an item (hereinafter, this item will be referred to as an "impact" item) indicating a relationship between the "club path (incidence angle) ψ" which is an index based on the incidence angle of the head of the golf club 3 at impact and the "relative face angle η" which is an index based on the inclination of the head at impact.

The second item may include an item regarding a speed of the golf club 3 at impact (at ball hitting). Hereinafter, the second item is assumed to include an item (hereinafter, this item will be referred to as a "speed" item) indicating a relationship among a "head speed" which is an index based on the speed of the golf club 3 at impact, a "sex", and the "type of golf club 3".

The plurality of items which are score calculation targets may also include a third item regarding the time at which a swing transitions from a backswing to a downswing, and the time of impact (the time of ball hitting). The third item may include an item indicating a relationship between a rotation angle about the long axis direction of the golf club 3 at the time (at top) at which a swing transitions from a backswing to a downswing and an inclination of the head of the golf club 3 at impact (at ball hitting). Hereinafter, the third item is assumed to include an item (hereinafter, this item will be referred to as a "rotation" item) indicating a relationship between the "shaft axis rotation angle $\theta_{top}$ at top" which is an index based on the rotation angle about the long axis direction of the golf club 3 at the top timing, and the "(absolute) face angle φ" which is an index based on the inclination of the head at impact.

The score calculation portion 311 performs a process of calculating a total score on the basis of the scores of the plurality of items. The processing section 31 transmits information regarding the scores or the total score of the plurality of items, calculated by the score calculation portion 311, to the swing analysis apparatus 20 via the communication section 32. In other words, the processing section 31 also functions as an output section which outputs the information regarding the scores (levels) or the total score of the plurality of items.

1-5. Swing Diagnosis Process

In the present embodiment, the processing section 31 of the swing diagnosis apparatus 30 performs a process of calculating scores and a total score of a plurality of items indicating features of a swing as a swing analysis process.

A detailed description will be made of a method of calculating a score of each item and a method of calculating a total score in the score calculation portion 311 of the processing section 31.

Calculation of Score of "V Zone" Item

The score calculation portion 311 calculates a score of the "V zone" item depending on in which regions head positions at halfway back and halfway down are included among a plurality of regions determined based on the shaft plane SP and the Hogan plane HP (V zone).

Figures 23, 24:
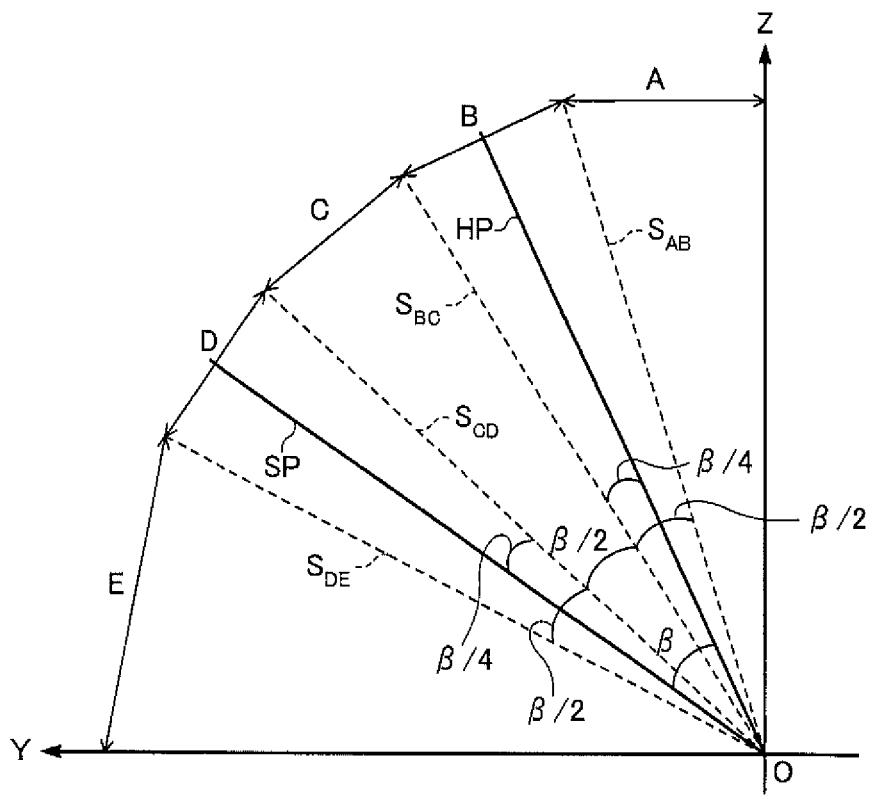
FIG. 23 is a diagram illustrating examples of relationships among the shaft plane and the Hogan plane, and a plurality of regions.
FIG. 24 is a diagram illustrating an example of a V zone score table.

FIG. 23 is a diagram illustrating examples of relationships among the shaft plane SP and the Hogan plane HP (V zone), and a plurality of regions. FIG. 23 illustrates relationships among the shaft plane SP, the Hogan plane HP, and five regions A to E when viewed from a negative side of the X axis (when projected onto the YZ plane). The region B is a predetermined space including the Hogan plane HP, and the region D is a predetermined space including the shaft plane SP. The region C is a space interposed between the region B and the region D (a space between an interface $S_{BC}$ with region B and an interface $S_{CD}$ with the region D). The region A is a space in contact with the region B in an interface SA on an opposite side to the region C. The region E is a space in contact with the region D in an interface $S_{DE}$ on an opposite side to the region C.

There may be various methods of setting the interface $S_{AB}$, the interface $S_{BC}$, the interface $S_{CD}$, and the interface $S_{DE}$. As an example, the interfaces may be set so that, on the YZ plane, the Hogan plane HP is located exactly at the center of the interface $S_{AB}$ and the interface $S_{BC}$, the shaft plane SP is located exactly at the center of the interface $S_{CD}$ and the interface $S_{DE}$, and angles of the region B, the region C, and the region D about the origin O (X axis) are the same as each other. In other words, with respect to the first angle β formed between the shaft plane SP and the Hogan plane HP, if each of angles formed between the Hogan plane HP, and the interface $S_{AB}$ and the interface $S_{BC}$ is set to β/4, and each of angles formed between the shaft plane SP, and the interface $S_{CD}$ and the interface $S_{DE}$ is set to β/4, angles of the region B, the region C, and the region D are all set to β/2.

Since a swing that causes a Y coordinate of a head position at halfway back or halfway down to be negative cannot be expected, an interface of the region A opposite to the interface $S_{AB}$ is set in the XZ plane in FIG. 23. Similarly, a swing that causes a Z coordinate of a head position at halfway back or halfway down to be negative cannot be expected, and an interface of the region E opposite to the interface $S_{DE}$ is set in the XY plane. Of course, an interface of the region A or the region E may be set so that an angle of the region A or the region E about the origin O (X axis) is the same as angles of the region B, the region C, and the region D.

Specifically, first, the score calculation portion 311 sets the interface $S_{AB}$, the interface $S_B$, the interface $S_{CD}$, and the interface $S_{DE}$ of the regions A to E on the basis of coordinates of each of the four vertices U1, U2, S1, and S2 of the shaft plane SP and coordinates of each of the four vertices U1, U2, H1, and H2 of the Hogan plane HP, included in data (selected swing analysis data 248) regarding a swing. Next, the score calculation portion 311 determines in which region of the regions A to E coordinates of a head position at halfway back and coordinates of a head position at halfway down included in the data (selected swing analysis data 248) regarding the swing are included. Information regarding a determination result thereof is transmitted to the swing analysis apparatus 20, and is used as the information regarding the "sex" and the "region in which a head position at halfway down is included" in the input data editing screen illustrated in FIG. 8. Thereafter, the score calculation portion 311 calculates a score corresponding to the determination result by referring to the V zone score table 342 and by using information regarding a "region in which a head position at halfway back is included" and a "region in which a head position at halfway down is included", included in the data (diagnosis target input data) regarding the swing.

In the present embodiment, as illustrated in FIG. 24, the V zone score table 342 defines a score for each combination of the region in which a head position at halfway back is included and the region in which a head position at halfway down is included. For example, in a case where a head position at halfway back is included in the region A, and a head position at halfway down is included in the region A, a score is pv1. Each of scores pv1 to pv25 illustrated in FIG. 24 is any one of, for example, 1 point to 5 points.

The score calculation portion 311 may calculate a lower score as a hit ball predicted on the basis of a relationship among the shaft plane SP, the Hogan plane HP, the head position at halfway back, and the head position at halfway down becomes more easily curved. The term "easily curved" may indicate that a trajectory after ball hitting is easily curved (easily sliced or hooked), and may indicate that a hit ball direction is easily deviated relative to a target direction (target line). Alternatively, the score calculation portion 311 may calculate a higher score as a hit ball more easily flies straight. The term "easily flies straight" may indicate that a trajectory after ball hitting is hardly curved (easily straightened), and may indicate that a hit ball direction is hardly deviated relative to a target direction (target line).

For example, in a case where a head position at halfway back is included in the region E, and a head position at halfway down is included in the region A, it is expected that a hit ball is easily curved, and thus the score calculation portion 311 calculates a relatively low score. Therefore, in the example illustrated in FIG. 24, pv21 may be 1 point which is the lowest score, for example, among 1 point to 5 points.

For example, in a case where a head position at halfway back and a head position at halfway down are all included in the region C, it is expected that a hit ball easily flies straight, and thus the score calculation portion 311 calculates a relatively high score (for example, 5 points maximum). Therefore, in the example illustrated in FIG. 24, pv13 may be 5 points which is the highest score, for example, among 1 point to 5 points.

Calculation of Score of "Rotation" Item

The score calculation portion 311 calculates a score of the "rotation" item depending on in which range among a plurality of ranges each of the shaft axis rotation angle $\theta_{top}$ at top and the face angle $\phi$ is included. Specifically, first, the score calculation portion 311 determines whether or not in which range each of the shaft axis rotation angle $\theta_{top}$ at top and the face angle $\phi$ included in data (target diagnosis input data) regarding a swing is included. Next, the score calculation portion 311 calculates a score corresponding to a determination result by referring to the rotation score table 343.

In the present embodiment, as illustrated in FIG. 25, the rotation score table 343 defines a score for each combination of a range in which the shaft axis rotation angle $\theta_{top}$ at top is included and a range in which the face angle $\phi$ is included. In the example illustrated in FIG. 25, a range in which the shaft axis rotation angle $\theta_{top}$ at top is included is classified into five ranges such as "less than $\theta 1$", "$\theta 1$ or more and less than $\theta 2$", "$\theta 2$ or more and less than $\theta 3$", "$\theta 3$ or more and less than $\theta 4$", and "$\theta 4$ or more". A range in which the face angle $\phi$ is included is classified into seven ranges such as "less than $\phi 1$", "$\phi 1$ or more and less than $\phi 2$", "$\phi 2$ or more and less than $\phi 3$", "$\phi 3$ or more and less than $\phi 4$", "$\phi 4$ or more and less than $\phi 5$", "$\phi 5$ or more and less than $\phi 6$", and "$\phi 6$ or more". For example, in a case where the shaft axis rotation angle $\theta_{top}$ at top is included in the range of "less than $\theta 1$", and the face angle $\phi$ is included in the range of "less than $\phi 1$", a score is pr1. Each of scores pr1 to pr35 illustrated in FIG. 25 is any one of, for example, 1 point to 5 points.

The score calculation portion 311 may calculate a lower score as a hit ball predicted on the basis of a relationship between the shaft axis rotation angle $\theta_{top}$ at top and the face angle $\phi$ becomes more easily curved.

For example, since the face surface of the golf club 3 is considerably open in a state where the shaft axis rotation angle $\theta_{top}$ at top is extremely large, it is expected that the face surface is not completely returned to a square at impact, and thus a hit ball is easily curved. A state in which the face angle $\phi$ is extremely large is a state in which the face surface at impact is considerably open, and a state in which the face angle $\phi$ is extremely small (a negative state in which an absolute value thereof is great) is a state in which the face surface at impact is considerably closed. In either state, it is expected that a hit ball is easily curved. In other words, for example, in a case where the shaft axis rotation angle $\theta_{top}$ is included in the range of "$\phi 4$ or more", and the face angle $\phi$ is included in the range of "less than $\phi 1$" or "$\phi 6$ or more", it is expected that a hit ball is easily curved, and thus the score calculation portion 311 calculates a relatively low score. Therefore, in the example illustrated in FIG. 25, pr29 or pr35 may be 1 point which is the lowest score, for example, among 1 point to 5 points.

For example, if the shaft axis rotation angle $\theta_{top}$ at top is small, it is expected that the face surface is completely returned to the square at impact, and thus a hit ball easily flies straight. If the face angle $\phi$ is close to 0°, the face surface at impact is close to the square, and thus it is expected that a hit ball easily flies straight. In other words, in a case where the shaft axis rotation angle $\theta_{top}$ is included in the range of "less than $\theta 1$", and the face angle $\phi$ is included in the range of "$\phi 3$ or more and less than $\phi 4$", it is expected that a hit ball easily flies straight, and thus the score calculation portion 311 calculates a relatively high score (for example, 5 points maximum). Therefore, in the example illustrated in FIG. 25, pr4 may be 5 points which is the highest score, for example, among 1 point to 5 points.

Calculation of Score of "Impact" Item

The score calculation portion 311 calculates a score of the "impact" item depending on in which range among a plurality of ranges each of the club path (incidence angle) ψ and the relative face angle η is included. Specifically, first, the score calculation portion 311 determines whether or not in which range the club path (incidence angle) ψ included in data (target diagnosis input data) regarding a swing is included. The score calculation portion 311 calculates the relative face angle η by subtracting the club path (incidence angle) ψ from the face angle φ included in the data (diagnosis target input data) regarding the swing (refer to FIG. 18), and determines in which range the relative face angle η is included. Next, the score calculation portion 311 calculates a score corresponding to a determination result by referring to the impact score table 344.

In the present embodiment, as illustrated in FIG. 26, the impact score table 344 defines a score for each combination of a range in which the relative face angle η is included and a range in which the club path (incidence angle) ψ is included. In the example illustrated in FIG. 26, a range in which the relative face angle η is included is classified into five ranges such as "η1 or more", "less than η1 and η2 or more", "less than η2 and η3 or more", "less than η3 and η4 or more", and "less than η4". A range in which the club path (incidence angle) ψ is included is classified into five ranges such as "less than ψ1", "ψ1 or more and less than ψ2", "ψ2 or more and less than ψ3", "ψ3 or more and less than ψ4", and "ψ4 or more". For example, in a case where the relative face angle η is included in the range of "η1 or more", and the club path (incidence angle) w is included in the range of "less than ψ1", a score is pi1. Each of scores pi1 to pi25 illustrated in FIG. 26 is any one of, for example, 1 point to 5 points.

The score calculation portion 311 may calculate a lower score as a hit ball predicted on the basis of a relationship between the club path (incidence angle) ψ and the relative face angle η becomes more easily curved.

For example, a state in which the relative face angle η is extremely large is a state in which the face surface at impact is open, and a state in which the face angle φ is extremely small (a negative state in which an absolute value thereof is great) is a state in which the face surface at impact is considerably closed. In either state, it is expected that a hit ball is easily curved. For example, in a state in which the club path (incidence angle) ψ is extremely large, a trajectory of the head at impact becomes a considerably inside-out trajectory, and it is expected that a hit ball is easily curved. In a state in which the club path (incidence angle) ψ is extremely small (a negative state in which an absolute value thereof is great), a trajectory of the head at impact becomes a considerably outside-in trajectory, and it is expected that a hit ball is easily curved. In other words, for example, in a case where the relative face angle η is included in the range of "η1 or more" or "less than η4", and the club path (incidence angle) ψ is included in the range of "less than ψ1" or "ψ4 or more", it is expected that a hit ball is easily curved, and thus the score calculation portion 311 calculates a relatively low score. Therefore, in the example illustrated in FIG. 26, pi1, pi5, pi21, and pi25 may be 1 point which is the lowest score, for example, among 1 point to 5 points.

For example, in a case where the relative face angle η is close to 0°, and the club path (incidence angle) W is close to 0°, the face surface at impact is close to the square, and a trajectory of the head at impact is nearly straight. Therefore, it is expected that a hit ball easily flies straight. In other words, in a case where the relative face angle η is included in the range of "less than η2 and η3 or more", and the club path (incidence angle) ψ is included in the range of "ψ2 or more and less than ψ3", it is expected that a hit ball easily flies straight, and thus the score calculation portion 311 calculates a relatively high score (for example, 5 points maximum). Therefore, in the example illustrated in FIG. 26, pi13 may be 5 points which is the highest score, for example, among 1 point to 5 points.

Calculation of Score of "Speed" Item

The score calculation portion 311 calculates a score of the "speed" item depending on in which range among a plurality of ranges a head speed is included. However, a head speed differs depending on males and females, and, generally, there is a tendency that a head speed of the males is high. A head speed differs depending on a driver or an iron, and, generally, there is a tendency that a head speed of the driver is high. Thus, it is preferable to select a plurality of set ranges for classifying a head speed on the basis of the sex or the type of golf club. Specifically, first, the score calculation portion 311 determines whether the user 2 is a male or a female, and whether the golf club 3 which is used is a driver or an iron, on the basis of information regarding the sex of the user 2 and information regarding the type of golf club 3 included in data (selected swing analysis data 248 or the like) regarding a swing. Information regarding a determination result is transmitted to the swing analysis apparatus 20, and is used as the information regarding a "sex" and the "type of golf club" on the input data editing screen illustrated in FIG. 8. Then, the score calculation portion 311 selects of a plurality of set ranges for classifying a head speed by using information regarding the "sex" and the "type of golf club" included in data (diagnosis target input data) regarding a swing. Next, the score calculation portion 311 determines in which range among a plurality of ranges a head speed included in the data (diagnosis target input data) regarding the swing is included. Next, the score calculation portion 311 calculates a score corresponding to a determination result by referring to the speed score table 345. The score calculation portion 311 may calculate a lower score as a head speed becomes lower.

In the present embodiment, as illustrated in FIG. 27, the speed score table 345 defines a plurality of ranges which are set depending on a "male" or a "female", and a "driver" or an "iron", and a score of a range in which a head speed is included for each of the plurality of set ranges. In the example illustrated in FIG. 27, in a case of a "male" and a "driver", a range in which a head speed is included is classified into five ranges such as "less than vh1", "vh1 or more and less than vh2", "vh2 or more and less than vh3", "vh3 or more and less than vh4", and "vh4 or more". In a case of a "male" and an "iron", a range in which a head speed is included is classified into five ranges such as "less than vh5", "vh5 or more and less than vh6", "vh6 or more and less than vh7", "vh7 or more and less than vh8", and "vh8 or more". In a case of a "female" and a "driver", a range in which a head speed is included is classified into five ranges such as "less than vh11", "vh11 or more and less than vh12", "vh12 or more and less than vh13", "vh13 or more and less than vh14", and "vh14 or more". In a case of a "female" and an "iron", a range in which a head speed is included is classified into five ranges such as "less than vh15", "vh15 or more and less than vh16", "vh16 or more and less than vh17", "vh17 or more and less than vh18", and "vh18 or more". For example, in a case of a "male" and a "driver", if a head speed is included in the range of "less than vh1", a score is 1 point which is the lowest score among 1 point to 5 points. If a head speed is included in the range of "vh4 or more", a score is 5 points which is the highest score among 1 point to 5 points. For example, in a case of a "female" and an "iron", if a head speed is included in the range of "less than vh15", a score is 1 point which is the lowest score among 1 point to 5 points. If a head speed is included in the range of "vh18 or more", a score is 5 points which is the highest score among 1 point to 5 points.

Calculation of Score of "Swing Efficiency" Item

The score calculation portion 311 calculates a score of the "swing efficiency" item depending on in which range among a plurality of ranges each of the grip deceleration ratio $R_V$ and the grip deceleration time ratio $R_T$ is included. Specifically, first, the score calculation portion 311 determines whether or not in which range each of the grip deceleration ratio $R_V$ and the grip deceleration time ratio $R_T$ included in data (target diagnosis input data) regarding a swing is included. Next, the score calculation portion 311 calculates a score corresponding to a determination result by referring to the swing efficiency score table 346.

In the present embodiment, as illustrated in FIG. 28, the swing efficiency score table 346 defines a score for each combination of a range in which the grip deceleration ratio $R_V$ is included and a range in which the grip deceleration time ratio $R_T$ is included. In the example illustrated in FIG. 28, a range in which the grip deceleration ratio $R_V$ is included is classified into six ranges such as "nu1 or more", "less than nu1 and nu2 or more", "less than nu2 and nu3 or more", "less than nu3 and nu4 or more", "less than nu4 and nu5 or more" and "less than nu5". A range in which the grip deceleration time ratio $R_T$ is included is classified into six ranges such as "nup1 or more", "less than nup1 and nup2 or more", "less than nup2 and nup3 or more", "less than nup3 and nup4 or more", "less than nup4 and nup5 or more", and "less than nup5". For example, in a case where the grip deceleration ratio $R_V$ is included in the range of "nu1 or more", and the grip deceleration time ratio $R_T$ is included in the range of "nup1 or more", a score is ps1. Each of scores ps1 to ps36 illustrated in FIG. 28 is any one of, for example, 1 point to 5 points.

The score calculation portion 311 may calculate a higher score as swing efficiency predicted on the basis of the grip deceleration ratio $R_V$ and the grip deceleration time ratio $R_T$ becomes higher.

It is considered in a golf swing that, when the head is accelerated, the arms are decelerated by reducing forces of the arms in a downswing, and thus natural rotation of the golf club occurs, so that the shaft is accelerated. A tendency for the natural rotation of the golf club to occur can be understood depending on to what extent a speed of the grip is decelerated during a downswing. Therefore, it is expected that a highly efficient swing using natural rotation of the golf club can be realized as the grip deceleration ratio $R_V$ becomes higher. However, if a timing at which natural rotation of the golf club occurs is close to an impact timing, that is, the grip deceleration time ratio $R_T$ is low, impact occurs in a state in which the natural rotation of the golf club cannot be sufficiently used, and thus it cannot necessarily be said that a highly efficient swing is performed. In other words, for example, in a case where the grip deceleration ratio $R_V$ is included in the range of "nu1 or more", and the grip deceleration time ratio $R_T$ is included in the range of "nup1 or more", it is expected that swing efficiency is high, and thus the score calculation portion 311 calculates a relatively high score. For example, in a case where the grip deceleration ratio $R_V$ is included in the range of "less than nu5", and the grip deceleration time ratio $R_T$ is included in the range of "less than nup5", it is expected that swing efficiency is low, and thus the score calculation portion 311 calculates a relatively low score. Therefore, in the example illustrated in FIG. 28, pa1 may be 5 points which is the highest score, for example, among 1 point to 5 points, and ps36 may be 1 point which is the lowest score, for example, among 1 point to 5 points.

Calculation of Total Score

The score calculation portion 311 calculates a total score on the basis of the score of the "V zone" item, the score of the "rotation" item, the score of the "impact" item, the score of the "speed" item, and the score of the "swing efficiency" item.

For example, in a case where a score of each item is 5 points maximum, if a maximum of a total score is 100 points, the score calculation portion 311 may multiply the score of each item by 4 so that 20 points maximum is obtained, and may add all the scores together so as to calculate a total score. In the swing diagnosis screen illustrated in FIG. 9, a score of 5 points maximum of each item is displayed as a radar chart, and the score of each item is multiplied by 4, and 64 points obtained by adding all the scores together is a total score.

For example, the score calculation portion 311 may increase a weight of a highly important item in diagnosis (evaluation) of a swing and may add scores of the items together so as to calculate a total score.

Procedures of Swing Diagnosis Process (Swing Diagnosis Method)

Figure 29:
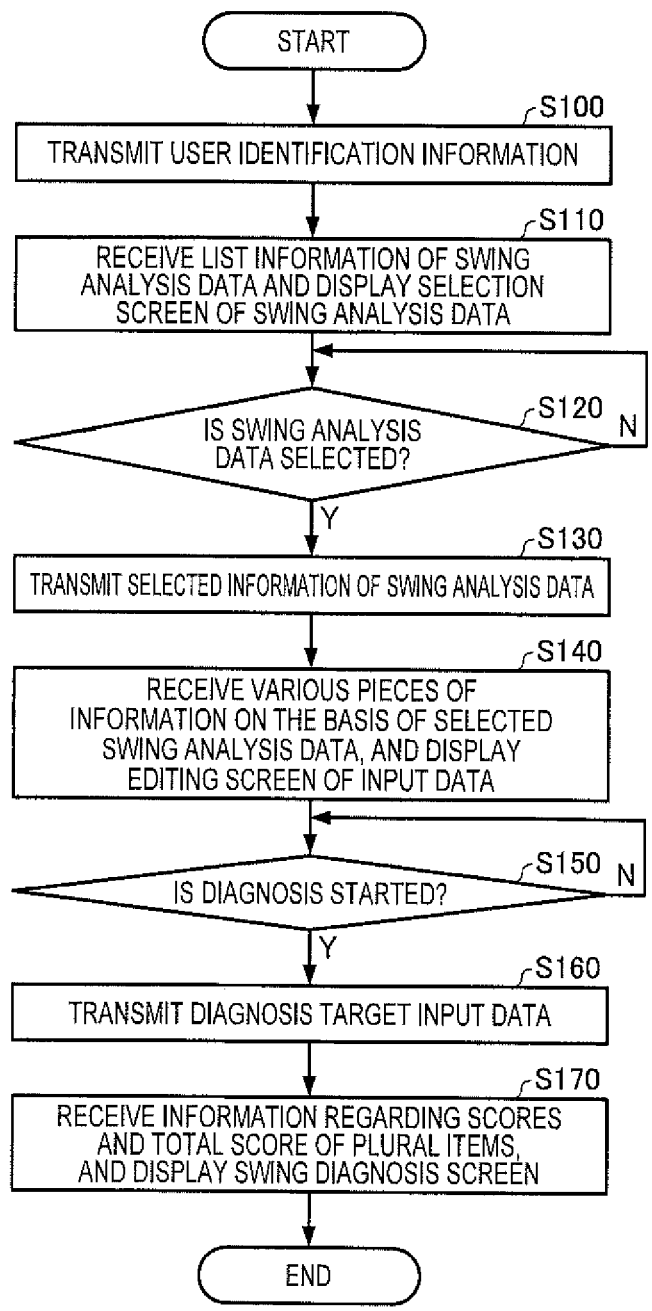
FIG. 29 is a flowchart illustrating examples of procedures of a process performed by the swing analysis apparatus in relation to a swing diagnosis process.
Figure 30:
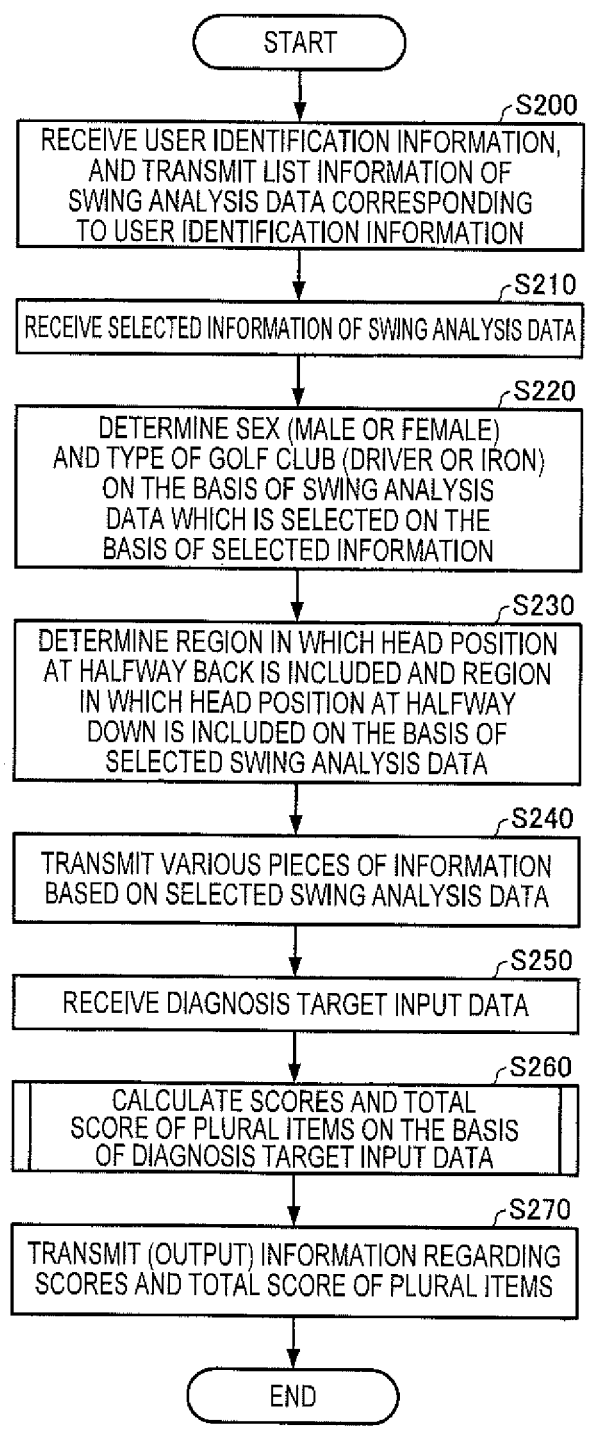
FIG. 30 is a flowchart illustrating examples of procedures of the swing diagnosis process (swing diagnosis method).

FIG. 29 is a flowchart illustrating examples of procedures of a process performed by the processing section 21 of the swing analysis apparatus 20 in relation to the swing diagnosis process. FIG. 30 is a flowchart illustrating examples of procedures of the swing diagnosis process (swing diagnosis method) performed by the processing section 31 of the swing diagnosis apparatus 30. The processing section 31 (an example of a computer) of the swing diagnosis apparatus 30 performs the swing diagnosis process, for example, according to the procedures of the flowchart of FIG. 30 by executing the swing diagnosis program 340 stored in the storage section 34. Hereinafter, the flowcharts of FIGS. 29 and 30 will be described.

First, the processing section 21 of the swing analysis apparatus 20 transmits user identification information allocated to the user 2, to the swing diagnosis apparatus 30 (step S100 in FIG. 29).

Next, the processing section 31 of the swing diagnosis apparatus 30 receives the user identification information, and transmits list information of the swing analysis data 248 corresponding to the user identification information (step S200 in FIG. 30).

Next, the processing section 21 of the swing analysis apparatus 20 receives the list information of the swing analysis data 248, and displays a selection screen (FIG. 7) of the swing analysis data on the display section 25 (step S110 in FIG. 29).

The processing section 21 of the swing analysis apparatus 20 waits for the swing analysis data 248 to be selected on the selection screen of the swing analysis data (N in step S120 in FIG. 29), and transmits selected information of the swing analysis data to the swing diagnosis apparatus 30 (step S130 in FIG. 29) if the information is selected (Y in step S120 in FIG. 29).

Next, the processing section 31 of the swing diagnosis apparatus 30 receives the selected information of the swing analysis data (step S210 in FIG. 30), and determines the sex (a male or a female) and the type of golf club (a driver or an iron) on the basis of the swing analysis data 248 which is selected on the basis of the selected information (step S220 in FIG. 30).

The processing section 31 of the swing diagnosis apparatus 30 determines a region in which a head position at halfway back is included and a region in which a head position at halfway down is included on the basis of the selected swing analysis data 248 (step S230 in FIG. 30).

Next, the processing section 31 of the swing diagnosis apparatus 30 transmits various pieces of information based on the selected swing analysis data (step S240 in FIG. 30). The various pieces of information based on the selected swing analysis data include the determination result in step S220, the determination result in step S230, and information regarding some index values (the face angle $\phi$, the club path (incidence angle) $\psi$, the shaft axis rotation angle $\theta_{top}$ at top, the head speed, the grip deceleration ratio $R_V$, and the grip deceleration time ratio $R_T$) included in the selected swing analysis data 248.

Next, the processing section 21 of the swing analysis apparatus 20 receives the various pieces of information based on the selected swing analysis data 248, and displays an editing screen (FIG. 8) of input data on the display section 25 (step S140 in FIG. 29).

The processing section 21 of the swing analysis apparatus 20 waits for a diagnosis starting operation to be performed on the editing screen of input data (N in step S150 in FIG. 29), and transmits diagnosis target input data to the swing diagnosis apparatus 30 (step S160 in FIG. 29) if the diagnosis starting operation is performed (Y in step S150 in FIG. 29).

Next, the processing section 31 of the swing diagnosis apparatus 30 receives the diagnosis target input data (step S250 in FIG. 30), and calculates scores and a total score of a plurality of items on the basis of the diagnosis target input data (step S260 in FIG. 30).

Next, the processing section 31 of the swing diagnosis apparatus 30 transmits (outputs) information regarding the scores and the total score of the plurality of items to the swing analysis apparatus 20 (step S270 in FIG. 30), and finishes the swing diagnosis process.

The processing section 21 of the swing analysis apparatus 20 receives the information regarding the scores and the total score of the plurality of items, displays the swing diagnosis screen (FIG. 9) on the display section 25 (step S170 in FIG. 29), and finishes the process.

In the flowchart of FIG. 29, order of the respective steps may be changed as appropriate within an allowable range, some of the steps may be omitted or changed, and other steps may be added thereto. Similarly, in the flowchart of FIG. 30, order of the respective steps may be changed as appropriate within an allowable range, some of the steps may be omitted or changed, and other steps may be added thereto.

Figure 31:
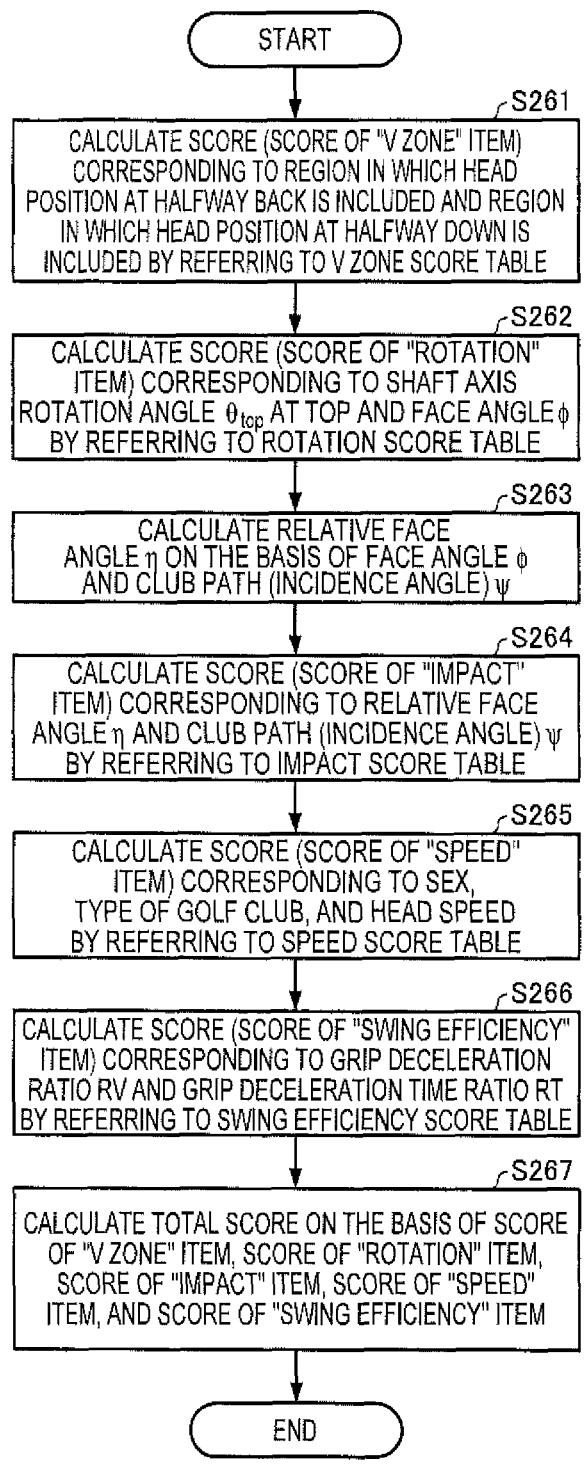
FIG. 31 is a flowchart illustrating examples of procedures of a process of calculating scores and a total score of a plurality of items.

FIG. 31 is a flowchart illustrating examples of procedures of a process (step S260 in FIG. 30) of calculating scores and a total score of a plurality of items in the processing section 31 (score calculation portion 311) of the swing diagnosis apparatus 30. Hereinafter, the flowchart of FIG. 31 will be described.

First, the processing section 31 calculates a score (a score of the "V zone" item) corresponding to a region in which a head position at halfway back is included and a region in which a head position at halfway down is included by referring to the V zone score table 342 stored in the storage section 34 (step S261).

Next, the processing section 31 calculates a score (a score of the "rotation" item) corresponding to the shaft axis rotation angle $\theta_{top}$ at top and the face angle $\phi$ by referring to the rotation score table 343 stored in the storage section 34 (step S262).

Next, the processing section 31 calculates the relative face angle $\eta$ on the basis of the face angle $\phi$ and the club path (incidence angle) $\psi$ (step S263).

Next, the processing section 31 calculates a score (a score of the "impact" item) corresponding to the relative face angle $\eta$ and the club path (incidence angle) $\psi$ by referring to the impact score table 344 stored in the storage section 34 (step S264).

Next, the processing section 31 calculates a score (a score of the "speed" item) corresponding to the sex, the type of golf club, and a head speed by referring to the speed score table 345 stored in the storage section 34 (step S265).

Next, the processing section 31 calculates a score (a score of the "swing efficiency" item) corresponding to the grip deceleration ratio $R_V$ and the grip deceleration time ratio $R_T$ by referring to the swing efficiency score table 346 stored in the storage section 34 (step S266).

Finally, the processing section 31 calculates a total score on the basis of the score of the "V zone" item calculated in step S261, the score of the "rotation" item calculated in step S262, the score of the "impact" item calculated in step S264, the score of the "speed" item calculated in step S265, and the score of the "swing efficiency" item calculated in step S266 (step S267).

1-6. Operations and Effects

As described above, in the swing diagnosis system 1 of the present embodiment, the swing diagnosis apparatus 30 calculates a score of a first item (the "V zone" item or the "swing efficiency" item) regarding at least one of a backswing and a downswing on the basis of data regarding a swing, so as to digitalize (level) and diagnose features of the backswing or the downswing. The swing diagnosis apparatus 30 also calculates a score of a second item (the "impact" item or the "speed" item) regarding impact on the basis of the data regarding the swing, so as to digitalize and diagnose features of the swing at impact. The swing diagnosis apparatus 30 calculates a score of a third item (the "rotation" item) regarding a top at which the backswing transitions to the downswing, and the impact on the basis of the data regarding the swing, so as to digitalize and diagnose features of the swing in which the time of starting the downswing and the time of finishing the downswing are taken into particular consideration. The swing analysis apparatus 20 displays the score of the first item (the "V zone" item or the "swing efficiency" item), the score of the second item (the "impact" item or the "speed" item), and the score of the third item (the "rotation" item) on the display section 25. Therefore, according to the swing diagnosis system 1 of the present embodiment, it is possible to digitalize and clearly show features of the swing till impact.

According to the swing diagnosis system 1 of the present embodiment, it is possible to digitalize and clearly show a feature of the swing based on relationships among the shaft plane SP (first virtual plane), the Hogan plane HP (second virtual plane), and positions of the head of the golf club 3 at desired timings (halfway back and halfway down) during the backswing and the downswing, by using the score of the "V zone" item.

According to the swing diagnosis system 1 of the present embodiment, it is possible to digitalize and clearly show a feature of the swing based on a relationship between a deceleration ratio and a deceleration period of the grip of the golf club 3 during a downswing in relation to a feature of the swing based on the swing efficiency by using a score of the "swing efficiency" item.

According to the swing diagnosis system 1 of the present embodiment, it is possible to digitalize and clearly show a feature of the swing based on a relationship between an incidence angle and an inclination of the head of the golf club 3 at impact by using the score of the "impact" item.

According to the swing diagnosis system 1 of the present embodiment, it is possible to digitalize and clearly show a feature of the swing based on a speed of the head of the golf club 3 at impact by using the score of the "speed" item.

According to the swing diagnosis system 1 of the present embodiment, it is possible to digitalize and clearly show a feature of the swing based on a relationship between a rotation angle about a shaft axis of the golf club 3 at the time of starting the downswing and an inclination of the head of the golf club 3 at impact by using the score of the "rotation" item.

Therefore, the user 2 can clearly recognize a level of the swing, strong points, weak points, problems, and the like in the swing thereof by using the scores of a plurality of items obtained as diagnosis results based on the swing analysis data 248.

In the swing diagnosis system 1 of the present embodiment, diagnosis target input data can be edited. Therefore, the user 2 can obtain information regarding which index is improved to what extent in order to overcome a weak point, by using scores of the plurality of items obtained as diagnosis results of input data in which some of the respective indexes of the swing are changed.

According to the swing diagnosis system 1 of the present embodiment, it is possible to reduce a load on the swing analysis apparatus 20 compared with a case where the swing analysis apparatus 20 also performs the swing diagnosis process, since the swing diagnosis apparatus 30 performs the swing diagnosis process (score calculation process).

According to the swing diagnosis system 1 of the present embodiment, since the swing analysis process and the swing diagnosis process are performed by using the sensor unit 10, a large apparatus such as a camera is not required to be used, and there is less restriction in a location where the user 2 performs a swing.

2. Modification Examples

The invention is not limited to the present embodiment, and may be variously modified within the scope of the spirit of the invention.

2-1. Swing Diagnosis System

In the embodiment, the swing diagnosis apparatus 30 may perform a part of a process (swing analysis process) performed by the swing analysis apparatus 20, and the swing analysis apparatus 20 may perform a part of a process (swing diagnosis process) performed by the swing diagnosis apparatus 30.

In the embodiment, the swing diagnosis system 1 is configured to include the sensor unit 10, the swing analysis apparatus 20, and the swing diagnosis apparatus 30, and may have other configurations. For example, the swing diagnosis system 1 may be configured to include a plurality of sensor units 10 and a plurality of swing analysis apparatuses 20.

Figure 32:
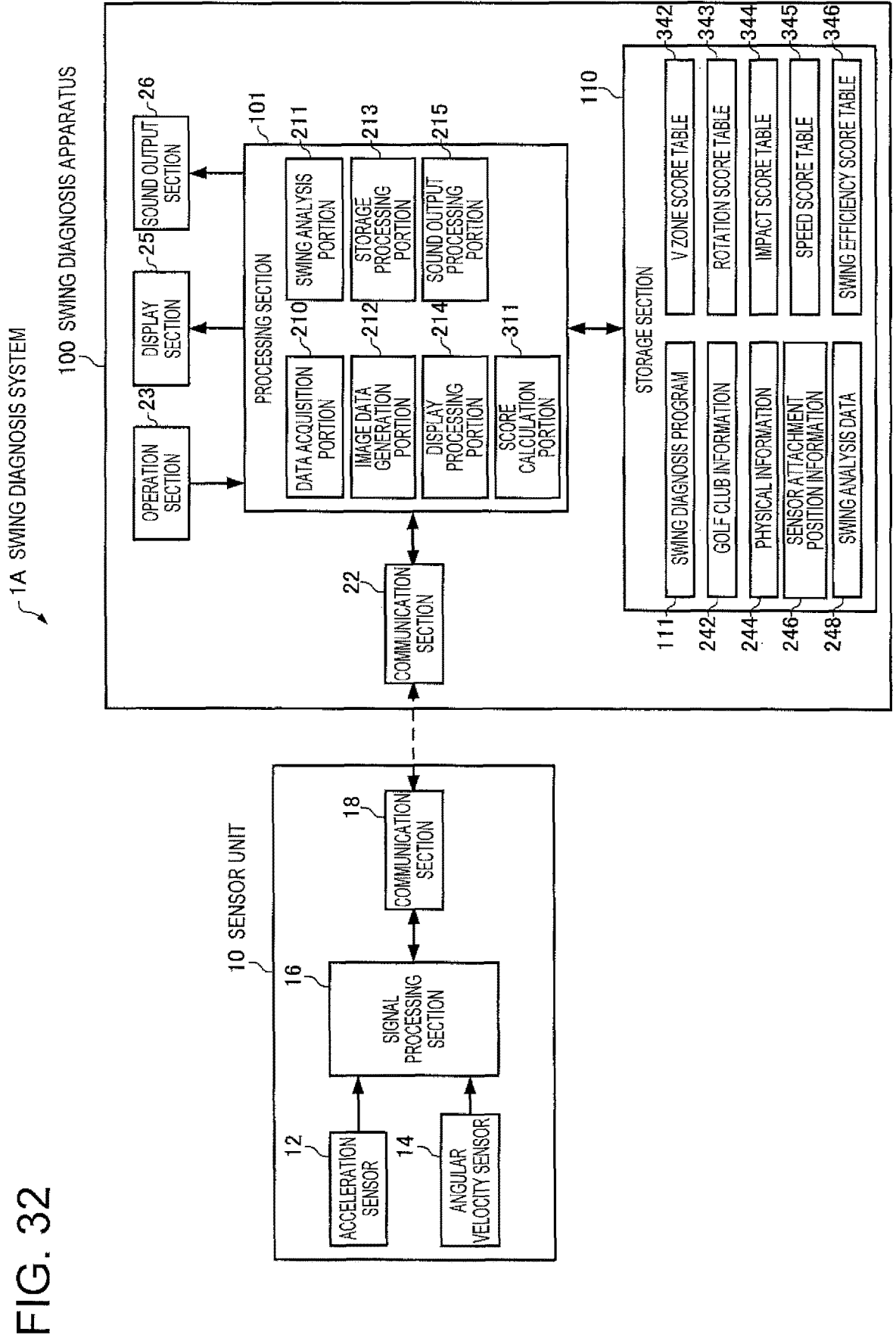
FIG. 32 is a diagram illustrating a configuration example of a swing diagnosis system according to a modification example.

For example, there may be a configuration in which a swing diagnosis system includes the sensor unit 10, and a swing diagnosis apparatus having both the functions of the swing analysis apparatus 20 and the functions of the swing diagnosis apparatus 30. FIG. 32 is a diagram illustrating a configuration example of the swing diagnosis system according to this modification example. In FIG. 32, the same constituent elements as those of the swing diagnosis system 1 of the embodiment are given the same reference numerals, and description thereof will be omitted. As illustrated in FIG. 32, a swing diagnosis system 1A of the modification example is configured to include a sensor unit 10 and a swing diagnosis apparatus 100.

The swing diagnosis apparatus 100 is configured to include a processing section 101, a communication section 22, an operation section 23, a storage section 110, a display section 25, and a sound output section 26. However, the swing diagnosis apparatus 100 may have a configuration in which some of the constituent elements are deleted or changed as appropriate, or may have a configuration in which other constituent elements are added thereto.

In the present modification example, the storage section 110 stores a swing diagnosis program 111 which is read by the processing section 101, and executes a swing diagnosis process including the swing analysis process in the embodiment. The swing diagnosis program 111 may be stored in a nonvolatile recording medium (computer readable recording medium) in advance. The swing diagnosis program 111 may be received by the processing section 101 from a server (not illustrated) via a network, and may be stored in the storage section 110.

In the present modification example, the storage section 110 stores golf club information 242, physical information 244, sensor attachment position information 246, and swing analysis data 248. The storage section 110 stores a V zone score table 342, a rotation score table 343, an impact score table 344, a speed score table 345, and a swing efficiency score table 346.

The processing section 101 (an example of a computer) executes the swing diagnosis program 111 so as to function as a data acquisition portion 210, a swing analysis portion 211, an image data generation portion 212, a storage processing portion 213, a display processing portion 214, a sound output processing portion 215, and a score calculation portion 311, and performs the swing diagnosis process. Consequently, the processing section 101 (particularly, the swing analysis portion 211) performs the same swing analysis process as in the embodiment so as to generate the swing analysis data 248 on the basis of measured data (an output signal from an inertial sensor) from the sensor unit 10. The processing section 101 (particularly, the score calculation portion 311) performs the same swing diagnosis process (score calculation process) as in the embodiment on the basis of the generated swing analysis data 248 which is data regarding a swing. The processing section 101 displays the swing diagnosis screen (FIG. 9) including calculated scores and a total score of a plurality of items on the display section 25.

The swing diagnosis system 1A (swing diagnosis apparatus 100) of the present modification example can also achieve the same operations and effects as the swing diagnosis system 1 (swing diagnosis apparatus 30) of the embodiment.

In the swing diagnosis system 1A illustrated in FIG. 32, the sensor unit 10 and the swing diagnosis apparatus 100 may perform communication with each other via a network. In other words, the swing diagnosis apparatus 100 may function as a server which performs the swing analysis process or the swing diagnosis process, and transmit (output) diagnosis result information (information regarding scores and a total score of a plurality of items) to an information terminal (for example, a smart phone or a personal computer) (not illustrated) via the network, so that the diagnosis result information may be displayed on a display section of the information terminal.

2-2. Swing Analysis Process

A plurality of sensor units 10 may be attached to the golf club 3 or parts such as the arms or the shoulders of the user 2, and the swing analysis portion 211 may perform a swing analysis process by using measured data from the plurality of sensor units 10.

In the embodiment, the swing analysis portion 211 calculates the third line segment 53 which is a third axis and the Hogan plane HP by using the physical information of the user 2, but a line segment and a plane obtained by rotating the second line segment 52 which is a second axis and the shaft plane SP by a predetermined first angle β (for example, 30°) about the X axis, respectively, may be used as the third line segment 53 and the Hogan plane HP.

In the embodiment, the swing analysis portion 211 detects impact by using the square root of the square sum as shown in Equation (2) as a combined value of three-axis angular velocities measured by the sensor unit, but, as a combined value of three-axis angular velocities, for example, a square sum of three-axis angular velocities, a sum or an average value of three-axis angular velocities, or the product of three-axis angular velocities may be used. Instead of a combined value of three-axis angular velocities, a combined value of three-axis accelerations such as a square sum or a square root of three-axis accelerations, a sum or an average value of three-axis accelerations, or the product of three-axis accelerations may be used.

2-3. Swing Diagnosis Process

In the embodiment, the score calculation portion 311 may calculate scores and a total score of a plurality of items on the basis of the selected swing analysis data 248 without displaying the input data editing screen as illustrated in FIG. 8. The score calculation portion 311 may calculate scores and a total score of a plurality of items on the basis of input data (for example, all indexes are manually input data) in which all values of indexes indicating features of a swing are pseudo-values.

In the embodiment, the score calculation portion 311 calculates scores of five items including the "V zone" item, the "rotation" item, the "impact" item, the "speed" item, and the "swing efficiency" item, but may not calculate scores of some of the items, and may calculate scores of other items. In the present embodiment, the score calculation portion 311 calculates a total score, but may not calculate a total score.

In the embodiment, the score calculation portion 311 calculates scores of a plurality of items by using various score tables, but may use equations instead of the score tables.

In the embodiment, the score calculation portion 311 may also function as the swing analysis portion 211, and may perform a swing diagnosis process (a swing analysis process and a score calculation process) including the swing analysis process on the basis of measured data (an output signal from an inertial sensor) from the sensor unit 10, which is data regarding a swing.

2-4. Others

In the embodiment, the acceleration sensor 12 and the angular velocity sensor 14 are built into and are thus integrally formed as the sensor unit 10, but the acceleration sensor 12 and the angular velocity sensor 14 may not be integrally formed. Alternatively, the acceleration sensor 12 and the angular velocity sensor 14 may not be built into the sensor unit 10, and may be directly mounted on the golf club 3 or the user 2. In the above-described embodiment, the sensor unit 10 and the swing analysis apparatus 20 are separately provided, but may be integrally formed so as to be attached to the golf club 3 or the user 2. The sensor unit 10 may have some of the constituent elements of the swing analysis apparatus 20 along with the inertial sensor (for example, the acceleration sensor 12 or the angular velocity sensor 14).

In the embodiment, the swing diagnosis system (swing diagnosis apparatus) diagnosing a golf swing has been exemplified, but the invention is applicable to a swing diagnosis system (swing diagnosis apparatus) diagnosing a swing in various sports such as tennis or baseball.

The above-described embodiment and modification examples are only examples, and the invention is not limited thereto. For example, the embodiment and the respective modification examples may be combined with each other as appropriate.

For example, the invention includes substantially the same configuration (for example, a configuration in which functions, methods, and results are the same, or a configuration in which objects and effects are the same) as the configuration described in the embodiment. The invention includes a configuration in which an inessential part of the configuration described in the embodiment is replaced with another part. The invention includes a configuration which achieves the same operation and effect or a configuration capable of achieving the same object as in the configuration described in the embodiment. The invention includes a configuration in which a well-known technique is added to the configuration described in the embodiment.

The entire disclosure of Japanese Patent Application No. 2015-148639 filed Jul. 28, 2015 is expressly incorporated by reference herein.

What is claimed is:

1. A swing diagnosis method comprising:
    grading, based on data regarding a swing, a plurality of items including (i) a first item regarding at least one of a backswing and a downswing and (ii) a second item regarding impact; and
    outputting the grading,
    wherein the grading is performed by assigning to each of the first and second items a score calculated from the data regarding the swing,
    the score of the first item is calculated using the first item and a first score table stored in a memory, and
    the score of the second item is calculated using the second item and a second score table stored in the memory.

2. The swing diagnosis method according to claim 1, wherein the first item includes an item indicating a relationship between (i) a position of a ball hitting portion of an exercise appliance at a first timing during the backswing with respect to at least one virtual plane and (ii) a position of the ball hitting portion at a second timing during the downswing with respect to the at least one virtual plane.

3. The swing diagnosis method according to claim 2, wherein the at least one virtual plane includes:
    a first virtual plane that is specified based on (i) a first axis along a target hit ball direction and (ii) a second axis along a longitudinal direction of the exercise appliance before starting the backswing; and
    a second virtual plane that forms a first angle with the first virtual plane.

4. The swing diagnosis method according to claim 1, wherein the first item includes an item regarding efficiency of the swing.

5. The swing diagnosis method according to claim 4, wherein the item regarding the swing efficiency is an item indicating a relationship between a deceleration amount and a deceleration period of a holding portion of an exercise appliance in the downswing.

6. The swing diagnosis method according to claim 1, wherein the second item includes an item indicating a relationship between an incidence angle of a ball hitting portion of an exercise appliance and an inclination of the ball hitting portion at impact.

7. The swing diagnosis method according to claim 1, wherein the second item includes an item regarding a speed of an exercise appliance at impact.

8. The swing diagnosis method according to claim 1, wherein the plurality of items include a third item regarding a time at which the backswing transitions to the downswing and a time of the impact.

9. The swing diagnosis method according to claim 8, wherein the third item includes an item indicating a relationship between (i) a rotation angle about a rotation axis of an exercise appliance at the time at which the backswing transitions to the downswing, a longitudinal direction of the exercise appliance being the rotation axis, and (ii) an inclination of a ball hitting portion of the exercise appliance at the time of the impact.

10. A non-transitory computer-readable recording medium recording a swing diagnosis program causing a computer to execute:
grading, based on data regarding a swing, a plurality of items including (i) a first item regarding at least one of a backswing and a downswing and (ii) a second item regarding impact; and
outputting the grading,
wherein the grading is performed by assigning to each of the first and second items a score calculated from the data regarding the swing,
the score of the first item is calculated using the first item and a first score table, and
the score of the second item is calculated using the second item and a second score table.

11. A swing diagnosis apparatus comprising:
a grading calculation section that grades, based on data regarding a swing, a plurality of items including (i) a first item regarding at least one of a backswing and a downswing and (ii) a second item regarding impact;
a memory; and
an output section that outputs the grading,
wherein the grading calculation section performs the grading by assigning to each of the first and second items a score calculated from the data regarding the swing,
the score of the first item is calculated using the first item and a first score table stored in the memory, and
the score of the second item is calculated using the second item and a second score table stored in the memory.

12. A swing diagnosis system comprising:
the swing diagnosis apparatus according to claim 11; and
an inertial sensor that measures the swing.

13. A swing diagnosis apparatus comprising a processor configured to:
grade, based on data regarding a swing, a plurality of items including (i) a first item regarding at least one of a backswing and a downswing and (ii) a second item regarding impact;
a memory; and
output the grading,
wherein the score of the first item is calculated using the first item and a first score table stored in the memory, and
the score of the second item is calculated using the second item and a second score table stored in the memory.

14. The swing diagnosis apparatus according to claim 13, wherein the first item includes an item indicating a relationship between (i) a position of a ball hitting portion of an exercise appliance at a first timing during the backswing with respect to at least one virtual plane and (ii) a position of the ball hitting portion at a second timing during the downswing with respect to the at least one virtual plane.

15. The swing diagnosis apparatus according to claim 14, wherein the at least one virtual plane includes:
a first virtual plane that is specified based on (i) a first axis along a target hit ball direction and (ii) a second axis along a longitudinal direction of the exercise appliance before starting the backswing; and
a second virtual plane that forms a first angle with the first virtual plane.

16. The swing diagnosis apparatus according to claim 13, wherein the first item includes an item regarding efficiency of the swing.

17. The swing diagnosis apparatus according to claim 16, wherein the item regarding the efficiency is an item indicating a relationship between a deceleration amount and a deceleration period of a holding portion of an exercise appliance in the downswing.

18. The swing diagnosis apparatus according to claim 13, wherein the second item includes an item indicating a relationship between an incidence angle of a ball hitting portion of an exercise appliance and an inclination of the ball hitting portion at impact.

19. The swing diagnosis apparatus according to claim 13, wherein the second item includes an item regarding a speed of an exercise appliance at impact.

20. The swing diagnosis apparatus according to claim 13, wherein the plurality of items include a third item regarding a time at which the backswing transitions to the downswing and a time of the impact.

21. The swing diagnosis apparatus according to claim 20, wherein the third item includes an item indicating a relationship between (i) a rotation angle about a rotation axis of an exercise appliance at the time at which the backswing transitions to the downswing, a longitudinal direction of the exercise appliance being the rotation axis, and (ii) an inclination of a ball hitting portion of the exercise appliance at the time of the impact.

* * * * *